(12) United States Patent (10) Patent No.: US 12,178,571 B2
Kovatchev et al. (45) Date of Patent: Dec. 31, 2024

(54) METHOD, SYSTEM AND COMPUTER PROGRAM PRODUCT FOR CGM-BASED PREVENTION OF HYPOGLYCEMIA VIA HYPOGLYCEMIA RISK ASSESSMENT AND SMOOTH REDUCTION INSULIN DELIVERY

(71) Applicant: UNIVERSITY OF VIRGINIA PATENT FOUNDATION, Charlottesville, VA (US)

(72) Inventors: Boris P. Kovatchev, Charlottesville, VA (US); Marc D. Breton, Charlottesville, VA (US); Stephen D. Patek, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 154 days.

(21) Appl. No.: 17/333,161

(22) Filed: May 28, 2021

(65) Prior Publication Data
US 2021/0282677 A1   Sep. 16, 2021

Related U.S. Application Data

(60) Continuation of application No. 17/070,245, filed on Oct. 14, 2020, now Pat. No. 11,723,562, which is a
(Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0002* (2013.01); *A61B 5/0004* (2013.01);
(Continued)

(58) Field of Classification Search
CPC . A61B 5/0004; A61B 5/14532; A61B 5/4839; A61B 5/7275; A61B 5/746; A61M 5/1723
See application file for complete search history.

(56) References Cited

U.S. PATENT DOCUMENTS 4,975,581 A   12/1990  Robinson et al.
5,036,861 A    8/1991  Sembrowich et al.
(Continued)

FOREIGN PATENT DOCUMENTS

EP       3703066 A1     9/2020
JP    2003528330 A      9/2003
(Continued)

OTHER PUBLICATIONS

Office Action (Communication) issued on Aug. 22, 2022, by the European Patent Office in corresponding European Patent Application No. 21213253.4. (2 pages).
(Continued)

*Primary Examiner* — Robert J Utama
*Assistant Examiner* — Hamza A Darb
(74) *Attorney, Agent, or Firm* — Buchanan Ingersoll & Rooney, PC

(57) ABSTRACT

An aspect of an embodiment or partial embodiment of the present invention (or combinations of various embodiments in whole or in part of the present invention) comprises, but not limited thereto, a method and system (and related computer program product) for continually assessing the risk of hypoglycemia for a patient and then determining what action to take based on that risk assessment. A further embodiment results in two outputs: (1) an attenuation factor to be applied to the insulin rate command sent to the pump (either via conventional therapy or via open or closed loop control) and/or (2) a red/yellow/green light hypoglycemia alarm providing to the patient an indication of the risk of
(Continued)

hypoglycemia. The two outputs of the CPHS can be used in combination or individually.

14 Claims, 17 Drawing Sheets

Related U.S. Application Data division of application No. 15/669,111, filed on Aug. 4, 2017, now Pat. No. 10,842,419, which is a continuation of application No. 14/015,831, filed on Aug. 30, 2013, now Pat. No. 9,750,438, which is a continuation of application No. 13/203,469, filed as application No. PCT/US2010/025405 on Feb. 25, 2010, now Pat. No. 8,562,587.

(60) Provisional application No. 61/263,932, filed on Nov. 24, 2009, provisional application No. 61/182,485, filed on May 29, 2009, provisional application No. 61/155,357, filed on Feb. 25, 2009.

(51) Int. Cl.
*A61M 5/172* (2006.01)
*G16H 20/17* (2018.01)
*G16H 40/63* (2018.01)
*G16H 40/67* (2018.01)
*G16H 50/50* (2018.01)

(52) U.S. Cl.
CPC .......... *A61B 5/4839* (2013.01); *A61B 5/7275* (2013.01); *A61B 5/746* (2013.01); *A61M 5/1723* (2013.01); *G16H 20/17* (2018.01); *G16H 40/63* (2018.01); *G16H 50/50* (2018.01); *G16H 40/67* (2018.01)

(56) References Cited

U.S. PATENT DOCUMENTS

| | | |
|---|---|---|
| 5,076,273 A | 12/1991 | Schoendorfer et al. |
| 5,086,229 A | 2/1992 | Rosenthal et al. |
| 5,139,023 A | 8/1992 | Stanley et al. |
| 5,140,985 A | 8/1992 | Schroeder et al. |
| 5,267,152 A | 11/1993 | Yang et al. |
| 5,279,543 A | 1/1994 | Glikfeld et al. |
| 6,144,869 A | 11/2000 | Berner et al. |
| 6,572,542 B1 | 6/2003 | Houben et al. |
| 6,923,763 B1 | 8/2005 | Kovatchev et al. |
| 7,025,425 B2 | 4/2006 | Kovatchev et al. |
| 7,060,059 B2 | 6/2006 | Keith et al. |
| 9,750,438 B2 | 9/2017 | Kovatchev et al. |
| 2004/0152622 A1 | 8/2004 | Keith et al. |
| 2005/0043598 A1* | 2/2005 | Goode, Jr. ............ A61B 5/1473 600/347 |
| 2005/0121322 A1 | 6/2005 | Say et al. |
| 2005/0171603 A1 | 8/2005 | Justin et al. |
| 2008/0154513 A1 | 6/2008 | Kovatchev et al. |
| 2008/0171913 A1 | 7/2008 | Randlov et al. |
| 2009/0001349 A1 | 1/2009 | Kahen |
| 2010/0256592 A1 | 10/2010 | Gerber et al. |
| 2010/0292634 A1 | 11/2010 | Bilmes et al. |
| 2021/0038132 A1 | 2/2021 | Kovatchev et al. |

FOREIGN PATENT DOCUMENTS

| | | |
|---|---|---|
| JP | 2008194452 A | 8/2008 |
| WO | 9600110 A1 | 1/1996 |
| WO | 0172208 A2 | 10/2001 |
| WO | 2008135329 A1 | 11/2008 |

OTHER PUBLICATIONS

Office Action (Notification of European Publication) issued on Jul. 20, 2022, by the European Patent Office in corresponding European Patent Application No. 21213253.4. (2 pages).
Refund of Fees issued on Jul. 22, 2022, by the European Patent Office in corresponding European Patent Application No. 21213253.4. (2 pages).
The extended European Search Report issued on Jul. 19, 2022, by the European Patent Office in corresponding European Application No. 21213253.4. (17 pages).
The extended European Search Report issued on Jul. 14, 2020, by the European Patent Office in corresponding European Application No. 20157783.0. (7 pages).
The extended European Search Report dated Sep. 16, 2013.
Buckingham, Bruce, et al., "Preventing Hypoglycemia Using Predictive Alarm Algorithms and Insulin Pump Suspension", Diabetes Technology & Therapeutics, vol. 11, No. 2, ISSN: 1520-9156, Q011 10.1089/dia.2008.0032, pp. 93-97, Feb. 1, 2009.
Communication pursuant to Article 94(3) EPC dated Oct. 29, 2018, issued in EP 10746831.6.
Kovatchev, et al., "Assessment of Risk for Severe Hypoglycemia Among Adults with IDDM", Diabetes Care, 21, pp. 1870-1875, 1998.
Notice of Allowance issued on Mar. 22, 2023, by the U.S. Patent and Trademark Office in U.S. Appl. No. 17/070,245.
Office Action (Communication) issued on Feb. 7, 2023, by the European Patent Office in corresponding European Patent Application No. 20 157 783.0. (11 pages).
Office Action (Communication) issued on Nov. 3, 2023, by the European Patent Office in corresponding European Patent Application No. 20 157 783.0. (11 pages).
The extended European Search Report issued on Nov. 7, 2023, by the European Patent Office in corresponding European Application No. 23179361.3. (7 pages).
Office Action (Communication) issued on Aug. 9, 2023, by the European Patent Office in corresponding European Patent Application No. 20 157 783.0. (11 pages).
Office Action issued on Sep. 19, 2023, by the U.S. Patent and Trademark Office in U.S. Appl. No. 18/325,564.
Office Action (Communication) issued on Dec. 15, 2023, by the European Patent Office in corresponding European Patent Application No. 21 213 253.4-1126. (8 pages).
Office Action (Summons to Attend Oral Proceedings) issued on Apr. 11, 2024, by the European Patent Office in corresponding European Patent Application No. 20 157 783.0. (11 pages).
Office Action (Summons to Attend Oral Proceedings) issued on Jun. 26, 2024, by the European Patent Office in corresponding European Patent Application No. 21 213 253.4. (11 pages).

* cited by examiner

METHOD, SYSTEM AND COMPUTER PROGRAM PRODUCT FOR CGM-BASED PREVENTION OF HYPOGLYCEMIA VIA HYPOGLYCEMIA RISK ASSESSMENT AND SMOOTH REDUCTION INSULIN DELIVERY

CROSS-REFERENCES TO RELATED APPLICATIONS

The present application is a divisional application of U.S. patent application Ser. No. 15/669,111, filed on Aug. 4, 2017, which claims priority from U.S. Provisional Application Ser. No. 61/155,357, filed Feb. 25, 2009, entitled "Method, System and Computer Program Product for CGM-Based Prevention of Hypoglycemia via Hypoglycemia Risk Assessment and Smooth Reduction Insulin Delivery," U.S. Provisional Application Ser. No. 61/182,485, filed May 29, 2009, entitled "Method, System and Computer Program Product for CGM-Based Prevention of Hypoglycemia via Hypoglycemia Risk Assessment and Smooth Reduction Insulin Delivery," and U.S. Provisional Application Ser. No. 61/263,932, filed Nov. 24, 2009, entitled "Method, System and Computer Program Product for CGM-Based Prevention of Hypoglycemia via Hypoglycemia Risk Assessment and Smooth Reduction Insulin Delivery," of which all of the disclosures are hereby incorporated by reference herein in their entirety.

The present application is related to International Patent Application Serial No. PCT/US2009/065725, filed Nov. 24, 2009, entitled "Method, System, and Computer Program Product for Tracking of Blood Glucose Variability in Diabetes from Data," the disclosure of which is hereby incorporated by reference herein in its entirety.

FIELD OF THE INVENTION

Some aspects of some embodiments of this invention are in the field of medical methods, systems, and computer program products related to managing the treatment of diabetic subjects, more particularly to glycemic analysis and control. Some embodiments of the invention relate to means for preventing hypoglycemia in a subject with diabetes.

BACKGROUND OF THE INVENTION

Since the earliest use of insulin for treatment of diabetes, efforts have been made to adjust the dosages of insulin based on clinical experience, and more particularly, measurements of the level of glucose. Initially glucose tests were done infrequently and in a standard clinical laboratory. With the advent of intermittent self-monitored glucose testing (i.e., self-monitoring blood glucose (SMBG)), such testing could be done by the patient and with a greater frequency at low cost. The application of information derived from more frequent glucose testing has allowed significantly better glucose control, and has lowered the occurrence of complications due to poor glycemic control. About a decade ago, the art incorporated continuous glucose monitors (i.e., continuous glucose monitoring (CGM)) that deliver glucose readings every few minutes. The results were displayed to the patient, and variously provided indications of the trend of the glucose as well as high-glucose and low-glucose alarms. Technological advances have been made also in the development of insulin pumps, which can replace multiple daily self-injections of insulin. These currently available devices can deliver precise insulin dosages, typically on a programmable schedule which may be adjustable on the basis of input from the user or healthcare professional, or on the basis of data from a continuous glucose monitor.

Basic algorithms have been developed that estimate an appropriate insulin dosing schedule based, for example, on patient weight, and these algorithms provide a reasonable first approximation of a clinically appropriate insulin-dosing schedule. There is, however, considerable variation among patients with regard to their metabolism and responsiveness to insulin.

Various approaches have been applied to making calculations that use continuous glucose monitor (CGM) data to improve or adjust insulin dosing. Artificial pancreas algorithms attempt to regulate blood glucose concentration in the face of meal disturbances and physical activity.

Other approaches, for example, provide for setting a basal insulin dose based on consideration of a patient's history, particularly glucose excursion data over a period of time.

Nevertheless, in spite of current aspects of diabetes care management, tight glycemic control has yet to be achieved. Insulin pump shut-off algorithms, as have been described in the prior art, use CGM data to inform the decision to completely stop the flow of insulin based on a prediction of hypoglycaemia. This approach has been shown to reduce the risk of nocturnal hypoglycaemia. A possible drawback is that the use of an on-off control law for basal insulin, similar to bang-bang or relay control, may induce undesired oscillations of plasma glucose. In fact, if the basal insulin is higher than that needed to keep the glycemic target, the recovery from hypoglycemia would be followed by application of the basal that will cause a new shut-off occurrence. The cycle of shut-off interventions yields an insulin square wave that induces periodic oscillation of plasma glucose.

BRIEF SUMMARY OF THE INVENTION

An aspect of an embodiment of the present invention seeks to, among other things, remedy the problems in the prior art. With the introduction of subcutaneous continuous glucose monitoring (CGM) devices that provide nearly real time measurement there is a need for achieving tight glycemic control. An aspect of an embodiment of the present invention CGM-Based Prevention of Hypoglycemia System (CPHS) and related method disclosed here serves to, but not limited thereto, provide an independent mechanism for mitigating the risk of hypoglycemia. Applications of this technology include, but not limited thereto, CGM-informed conventional insulin pump therapy, CGM-informed open-loop control systems, and closed-loop control systems. These systems may be most applicable to the treatment of Type 1 and Type 2 diabetes (T1DM and T2DM, respectively), but other applications are possible.

An aspect of an embodiment or partial embodiment of the present invention (or combinations of various embodiments in whole or in part of the present invention) comprises, but is not limited to, a method and system (and related computer program product) for continually assessing the risk of hypoglycemia for a patient and then determining what action to take based on that risk assessment. A further embodiment results in two outputs: (1) an attenuation factor to be applied to the insulin rate command sent to the pump (either via conventional therapy or via open or closed loop control) and/or (2) a red/yellow/green light hypoglycemia alarm providing to the patient an indication of the risk of hypoglycemia. The two outputs of the CPHS can be used in combination or individually.

An aspect of an embodiment of the present invention innovates in numerous ways on existing technologies by acting on the risk of hypoglycemia and not explicitly and exclusively on the glucose level. An aspect of an embodiment of the invention further innovates by gradually decreasing insulin levels, therefore avoiding under-insulinization of the patient and reducing the risk of hyperglycemia as compared to rigid pump shut-off algorithms. An aspect of an embodiment of the invention also uses insulin pump feedback to increase the accuracy of the hypoglycemia risk assessment. An aspect of an embodiment of the invention further integrates an alert system that not only informs the user that the system is actively preventing hypoglycemia but is also capable of requesting user intervention in case no amount of insulin.

An aspect of an embodiment of the CPHS (and related method) prevents hypoglycemia, rather than merely manipulating BG into a specific target or tight range.

An aspect of an embodiment of the present invention provides a method for preventing or mitigating hypoglycemia in a subject. The method may comprise the following: obtaining metabolic measurements associated with the subject; continuously assessing a risk of hypoglycemia based on the metabolic measurements; and evaluating the risk of hypoglycemia to determine one of the following outcomes 1) no action is needed, 2) attenuation of insulin delivery is needed, 3) additional intervention is needed, or 3) attenuation of insulin delivery and additional intervention are needed.

An aspect of an embodiment of the present invention provides a system for preventing or mitigating hypoglycemia in a subject. The system may comprise the following: an obtaining device for obtaining metabolic measurements associated with the subject; an assessment device for continuously assessing a risk of hypoglycemia based on the metabolic measurements; and an evaluation device for evaluating the risk of hypoglycemia to determine one of the following outcomes: 1) no action is needed, 2) attenuation of insulin delivery is needed, 3) additional intervention is needed, or 4) attenuation of insulin delivery and additional intervention are needed.

An aspect of an embodiment of the present invention provides a computer program product comprising a computer useable medium having a computer program logic for enabling at least one processor in a computer system to prevent or mitigate hypoglycemia in a subject. The computer logic may comprise the following: obtaining data of metabolic measurements associated with the subject; continuously assessing a risk of hypoglycemia based on the metabolic measurements; and evaluating the risk of hypoglycemia to determine one of the following outcomes: 1) no action is needed, 2) attenuation of insulin delivery is needed 3) additional intervention is needed, or 4) attenuation of insulin delivery and additional intervention are needed.

It should be appreciated that the continuous assessment may occur X times per second, where 1<X<1000 (as well as at a faster rate or frequency if desired or required). It should be appreciated that the continuous assessment may occur X times per hour, where 1<X<1000. It should be appreciated that the continuous assessment may occur X times per day, where 1<X<1000. The assessment can be made periodically or at time intervals where their duration and frequency can vary. As an example, the assessment may occur every minute or every few to several minutes. Another example of continuous assessment shall include any point in time where a sample (for example, but not limited thereto, BG, CGM samples, glucose measurements, etc.) or input (for example, but not limited thereto, basal rate change, bolus events acknowledged by the pump, etc.) is received that can be assessed. For instance, the risk assessment may be event driven. Also, it should be appreciated that a given day(s) can be skipped for conducting assessment activities or steps.

The foregoing and other objects, features and advantages of the present invention, as well as the invention itself, will be more fully understood from the following description of preferred embodiments, when read together with the accompanying drawings.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF THE INVENTION

Figure 1:
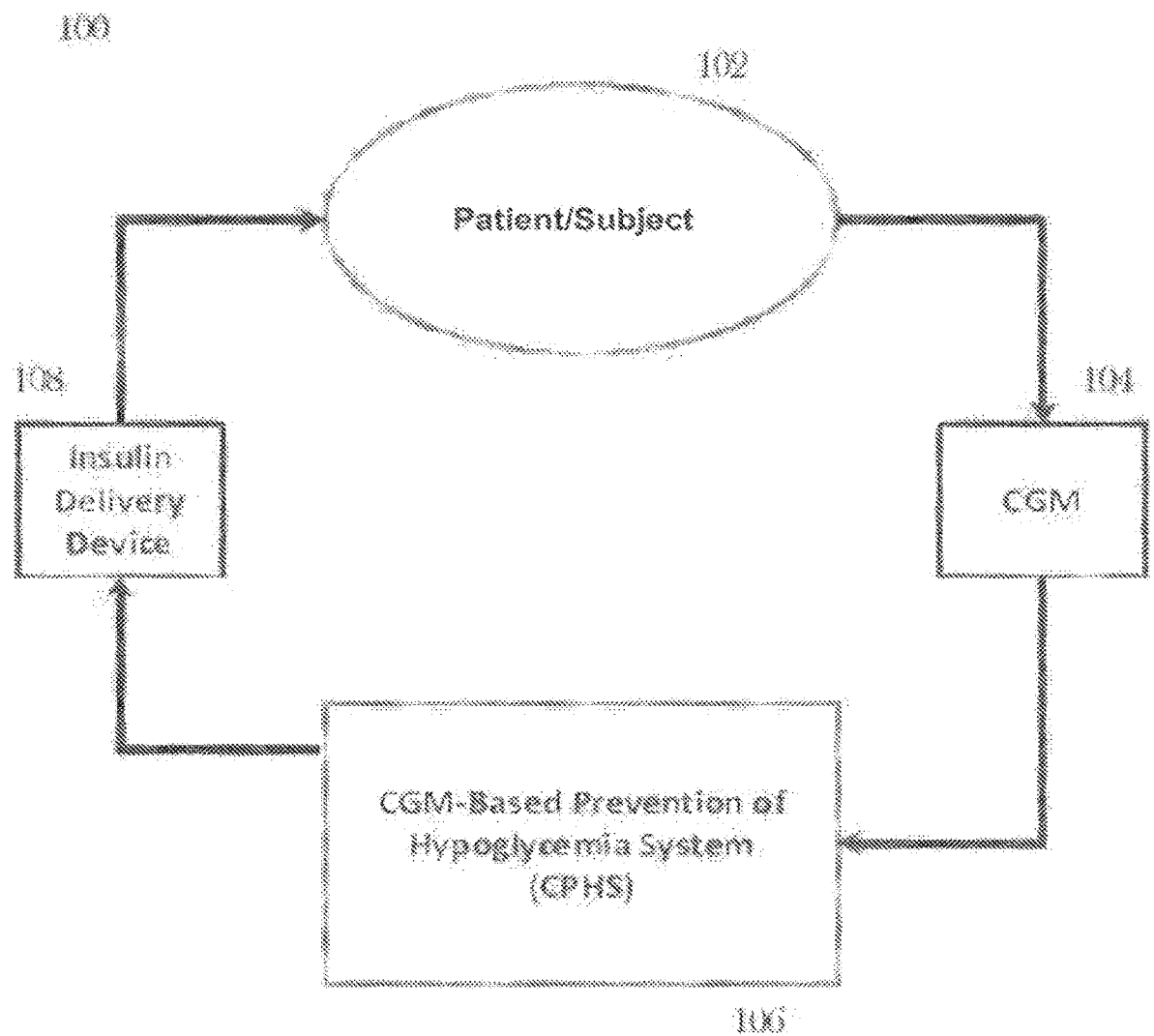
FIG. 1 schematically provides an exemplary embodiment of the CGM-based prevention of hypoglycemia system (CPHS).

An aspect of an embodiment of the CGM-Based Prevention of Hypoglycemia System (CPHS) (and related method and computer program product) presented here may utilize CGM data to continually assess the risk of hypoglycemia for the patient and then provides two outputs: (1) an attenuation factor to be applied to the insulin rate command sent to the pump (either via conventional therapy or via open or closed loop control) and/or (2) a red/yellow/green light hypoglycemia alarm providing to the patient an indication of the risk of hypoglycemia. The two outputs of the CPHS can be used in combination or individually.

The first section below presents the CPHS for the case where the only input to the system is CGM data.

The second section presents the CPHS for the case where, in addition to CGM data, the system receives as an input some external data, including insulin commands.

A distinguishing aspect of an embodiment of the present invention system, method and computer program product compared to other methods of hypoglycemia prevention, for example, but not limited thereto is its use of formal assessments of hypoglycemia risk, both in determining the appropriate attenuation of insulin and in producing the appropriate red/yellow/green signal.

Another aspect of an embodiment of the present invention is the attenuation function of the CPHS (and related method and computer program product), which adjusts the restriction of insulin as a smooth function of CGM measures, not abruptly, as in prior art pump-shutoff methods. In the following sections, a specific methodology based on a risk symmetrization function is presented. The same techniques could be used for other risk assessment techniques, including risk assessments that use other input signals such as meal acknowledgement information and indications of physical activity, as long as they vary smoothly as a function of CGM data. No other hypoglycemia prevention system relies on the use of risk assessments to produce a smoothly varying attenuation factor.

Another aspect of an embodiment of the present invention system, method and computer program product is the traffic signal abstraction for the hypoglycemia alarm system.

Before proceeding, it is important to note that conventional pump shutoff methods suffer from the complexity of deciding exactly when to shut off and exactly when to resume operation, with both decisions being significantly hampered by CGM noise and errors. Smooth adjustment of the restriction of insulin, as in the CPHS, accommodates CGM noise in a natural way. First, if there are spurious errors in the CGM signal, they can only become spurious errors in the degree of attenuation because there is never a point in time where a crisp attenuation decision has to be made. Next, systematic errors in the CGM signal are eventually accommodated by the system. For example, even if the CGM is reading high (indicating a higher blood glucose than is actually the case), a downward trend will eventually respond in a severe restriction of delivery of insulin.

CPHS With CGM Input Only

This section presents a basic form of an embodiment of the present invention in which only CGM data is used to prevent hypoglycemia, as illustrated in FIG. 1. It should be noted that the CPHS can function without any other input signals. This subsection explains how the CPHS would operate in a CGM-only configuration. Also included is an illustration of procedures by which the attenuation factor is computed and red/yellow/green light hypoglycemia alarms are generated (See FIG. 2).

FIG. 1 illustrates a first exemplary embodiment of the hypoglycemia prevention system 100. The subject, such as a patient 102 may be a diabetic subject who takes insulin to prevent complications arising from diabetes. Continuous Glucose Monitor (CGM) 104 collects information about the patient, specifically blood or interstitial glucose levels. The blood or interstitial glucose data is measured directly from the patient 102, without the inclusion of any intermediary or independent device. CPHS 106 takes as input the blood glucose data acquired by CGM 104. Based on this data, the CPHS 106 evaluates the risk of hypoglycemia. The risk corresponds to one or more actions to be taken, including taking no action, attenuating insulin delivery, and/or taking additional intervention. If the output of the CPHS 106 is to attenuate insulin delivery, the CPHS indicates to the insulin delivery device 108 to lower the amount of insulin delivered to the patient 102. It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

Figure 2:
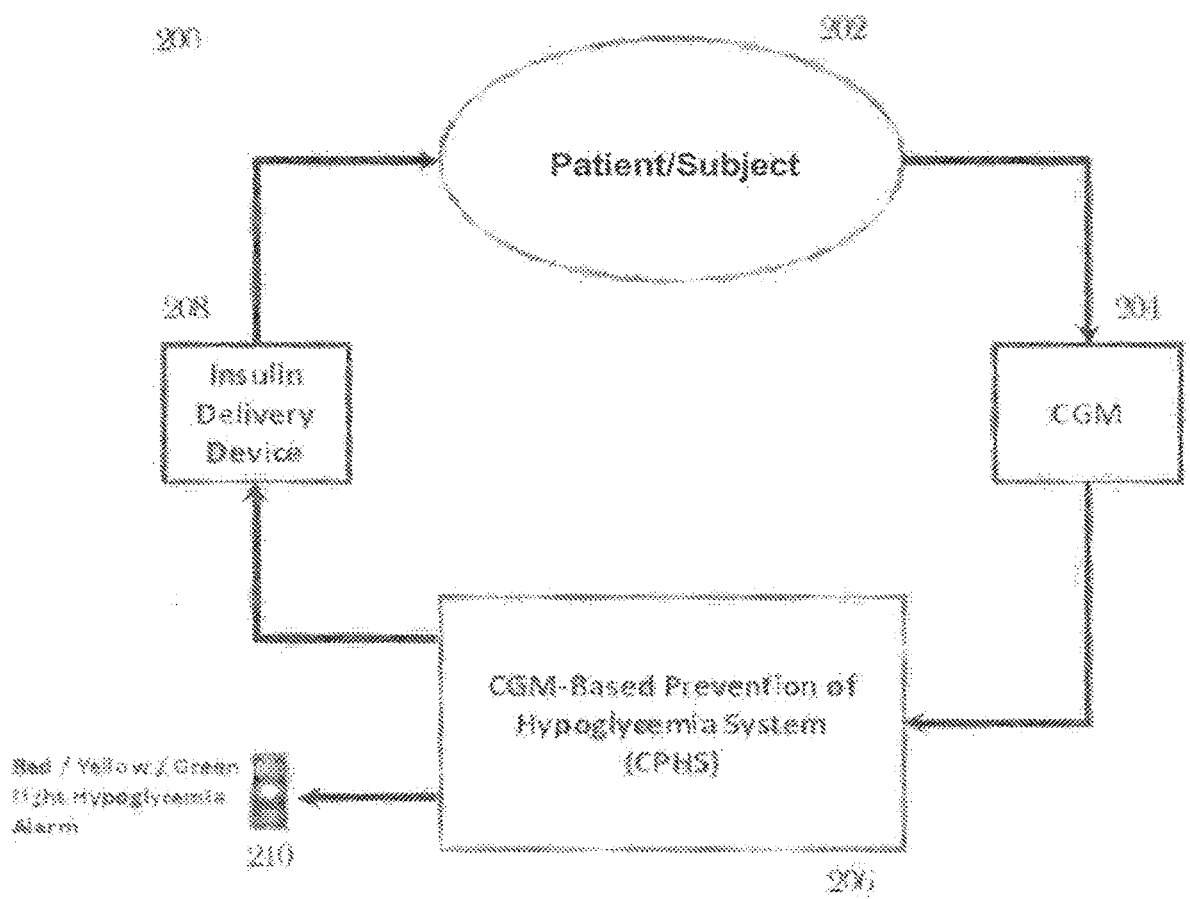
FIG. 2 schematically provides an exemplary embodiment of the CGM-based prevention of hypoglycemia system (CPHS).

FIG. 2 illustrates a second exemplary embodiment of the hypoglycemia prevention system 200. Again, a subject, such as a patient 202 is a diabetic subject and the CGM 204 collects information about the patient 202. The CPHS 206 takes as input the blood glucose data acquired by CGM 204. Based on this data, the CPHS 206 evaluates the risk of hypoglycemia and determines whether and what kind of action to take. These actions include taking no action, attenuating insulin delivery, and/or taking additional intervention. Depending on the risk of hypoglycemia, a visual indicator 210 displays a colored light. If there is no risk of hypoglycemia, the CPHS 206 will take no action and the visual indicator 210 will present a green light (or other type of indicator as desired or required). If the risk of hypoglycemia is low the CPHS 206 will attenuate insulin delivery and the visual indicator 210 will present a yellow light (or other type of indicator as desired or required). If the risk of hypoglycemia is high, the CPHS 206 will either (1) call for additional intervention, or (2) call for additional intervention and attenuate insulin delivery. In either case, the visual indicator, 210, will present a red light (or other type of indicator as desired or required).

It should be appreciated that any of the embodiments discussed herein may be intended for some sort or kind of visual tracking. However, it should be appreciated that information that is conveyed visually may be conveyed audibly and/or tactically (perceptible to the sense of touch) if desired or required. Accordingly, a audible and/or tactile scheme would be provided to convey or provide at least some or all of the aspects being conveyed visually or in combination therewith. Moreover, for example, audible signals may be provided in addition to or in concert or parallel with the visual information.

Figure 3:
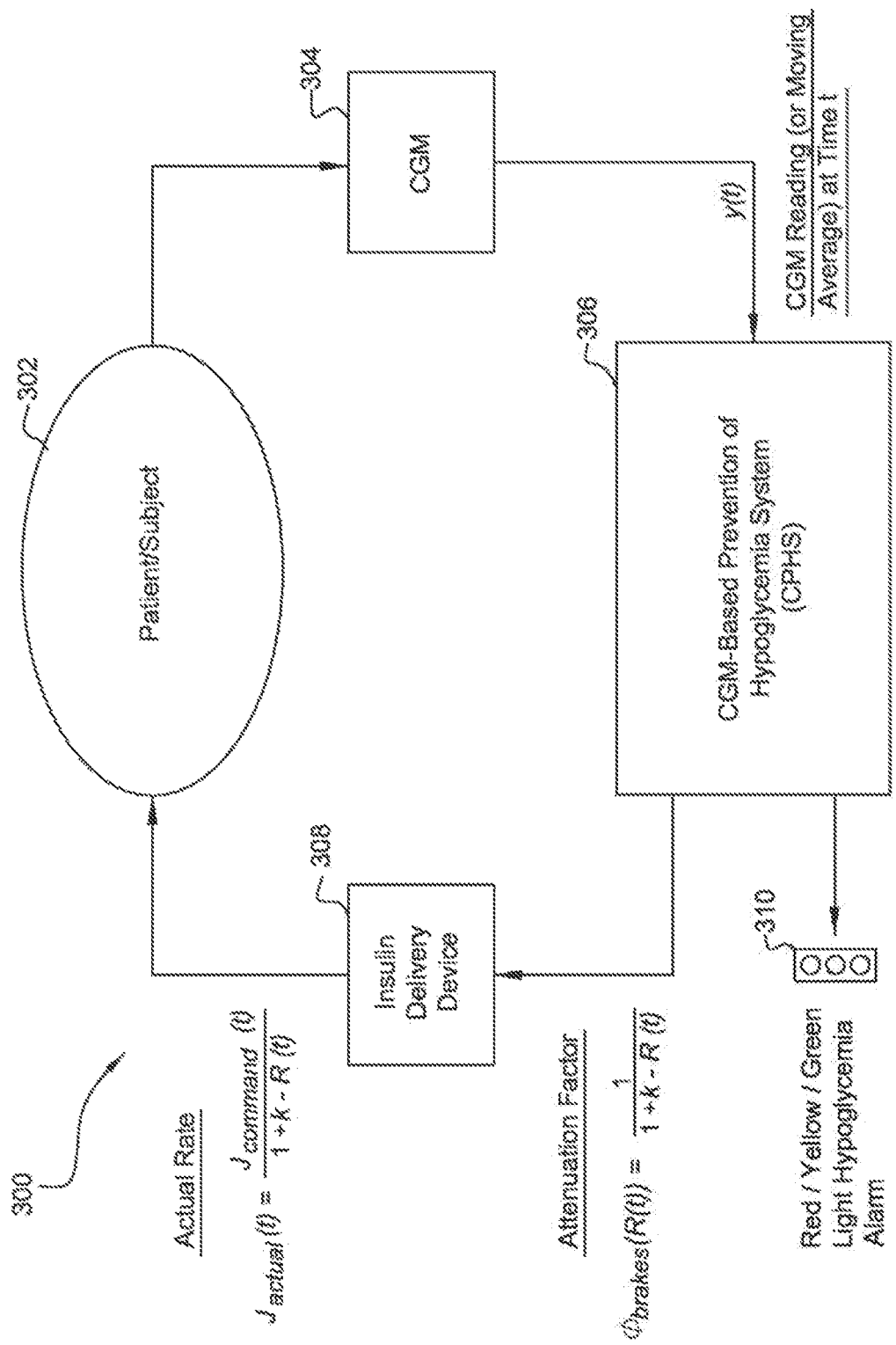
FIG. 3 schematically provides a more detailed exemplary embodiment of the CGM-based prevention of hypoglycemia system (CPHS) from FIG. 2.

FIG. 3 presents a more detailed view of the system illustrated in FIG. 2. As in the previous figures, the subject or patient 302 CGM 304, and insulin delivery device 306 are provided. The CPHS 308 uses CGM data, y(t), to compute an attenuation factor, $\phi_{bakes}(R(t))$, based on a risk of hypoglycemia assessment, R(t). The CPHS 308 may also or solely present to the user red, yellow, or green lights indicating the risk of hypoglycemia via visual indicator 310. The CPHS is designed to add a safety supervision function to different types of blood glucose management functions, including conventional therapy, open-loop and advisory mode systems, and closed loop systems. Keeping in mind that the subject or patient has ultimate authority over insulin boluses, the CPHS 306 serves to modify insulin rates by modifying the programmed rate of insulin injection, $J_{command}(t)$, in the insulin delivery device 308. This attenuation of insulin delivery is performed by multiplying the hypoglycemia attenuation factor by the programmed rate of insulin injection to determine an actual rate of insulin injection:

$$J_{actual}(t) = \phi_{brakes}(R(t)) \cdot J_{command}(t)$$

The attenuation factor output of the CGM-only CPHS is computed via an algorithmic process referred to as brakes. The brakes algorithm and method are designed to adjust insulin rate commands to the insulin pump to avoid hypoglycemia. A feature of an embodiment of the present invention is that brake action smoothly attenuates the patient's insulin delivery rate at the present time t by monitoring CGM and insulin pump data, assessing a measure of the patient's future risk of hypoglycemia R(t), and then computing an attenuation factor $\phi_{brakes}(R(t))$. The attenuation factor is computed as follows:

$$\phi_{brakes}(R(t)) = \frac{1}{1 + k \cdot R(t)}$$

where k is an aggressiveness parameter that may be adjusted to match the patient's physiology (i.e. according to the patient's insulin sensitivity).

As illustrated in FIG. 3, the attenuation factor would be used by the insulin delivery device 308 to compute reduced actual pump rate $J_{actual}(t)$ (U/hr) according to:

$$J_{actual}(t) = \phi_{brakes}(R(t)) \cdot J_{command}(t)$$

where $J_{actual}(t)$ is the attenuated insulin rate (U/hr) and $J_{command}(t)$ is the rate of insulin injection (U/hr) that the pump is set to administer.

In the CGM-only version of the CPHS, the risk assessment function R(t) is computed purely from CGM data, as follows. First, R(t) is computed as a sample average of raw risk values:

$$R(t) = \frac{1}{M} \sum_{\tau=0}^{M-1} \tilde{R}(t - \tau)$$

where M is the size of the moving average window for risk assessment and, for any stage 1, the raw risk value is computed as $$\tilde{R}(t) = \begin{cases} 10 \cdot [\gamma(\theta) \cdot (\ln(y(t))^{\alpha(\theta)} - \beta(\theta))]^2 & \text{if } 20 < y(t) < \theta \\ 100 & \text{if } y(t) \leq 20 \\ 0 & \text{otherwise.} \end{cases}$$

where y(t) (mg/dl) is either the most recent CGM sample or an average of recent CGM samples (e.g. moving average, exponentially weighted moving average, etc.) and the parameters $\alpha(\theta)$, $\beta(\theta)$, and $\gamma(\theta)$ are computed in advance based on a threshold glucose concentration, $\theta$ (mg/dl), which is specific to the embodiment of the CPHS. Note that $\theta$ is the glucose concentration below which the risk function will be positive, resulting in an attenuation factor $\phi_{brakes}(R(t)) < 1$.

Values for parameters $\alpha(\theta)$, $\beta(\theta)$, and $\gamma(\theta)$ are listed for various threshold glucose concentrations, $\theta$, in Table 1 below.

TABLE 1

| Threshold Glucose Concentration θ (mg/dl) | α(θ) | β(θ) | γ(θ) |
|---|---|---|---|
| 90 | 0.384055 | 1.78181 | 12.2688 |
| 100 | 0.712949 | 2.97071 | 4.03173 |
| 112.5 | 1.08405 | 5.381 | 1.5088 |
| 120 | 1.29286 | 7.57332 | 0.918642 |
| 160 | 2.29837 | 41.8203 | 0.10767 |
| 200 | 3.24386 | 223.357 | 0.0168006 |

The choice of values of k, M, and $\theta$ depends upon the embodiment of the CPHS. In some embodiments, these parameters will be fixed at preset values, with M typically being set to one for embodiments in which CGM values arrive frequently, say every minute. In other embodiments, k, M, and $\theta$ will be manually set to fixed values in concert with the patient's physician (e.g. according to the patient's insulin sensitivity and eating behavior) or input by the patient or other individual providing the input. In yet other embodiments, the parameter values will be set according to regression formulas involving the patient's physical characteristics (e.g. body weight, total daily insulin TDI (U), carbohydrate ratio, correction factor CF (mg/dl/U), age, etc.). One such regression formula for k follows:

$$k = \exp(-0.7672 - 0.0091 \cdot TDI + 0.0449 \cdot CF)$$

Experiments run on the FDA-accepted T1DM simulator at the University of Virginia show that the performance of the brakes varies smoothly as a function of k and $\theta$, and, while setting these parameters optimally leads to the best ability to prevent hypoglycemia, adverse events do not arise when non-optimal values are chosen.

Testing was completed to determine the viability of this embodiment of the invention. The following results show the efficacy of the brakes algorithm and methodology for the embodiment where k=1, M=1, and $\theta$=120 (mg/dl). The results are obtained from the FDA-accepted UVA/U. Padova Metabolic Simulator. Some T1DM patients experience highly variable insulin sensitivity (e.g. after physical activity), and, for such a patient, it can happen that his/her basal rate of insulin delivery, which is tuned to achieve fasting euglycemia under normal circumstances, is from time to time suddenly too high, putting the patient at risk of hypoglycemia. For these patients, an embodiment of the CGM-only CPHS with k=1, M=1, and $\theta$=120 (mg/dl) will successfully mitigate the risk of hypoglycemia, as illustrated in the simulation results of FIG. 6.

Figure 6A:
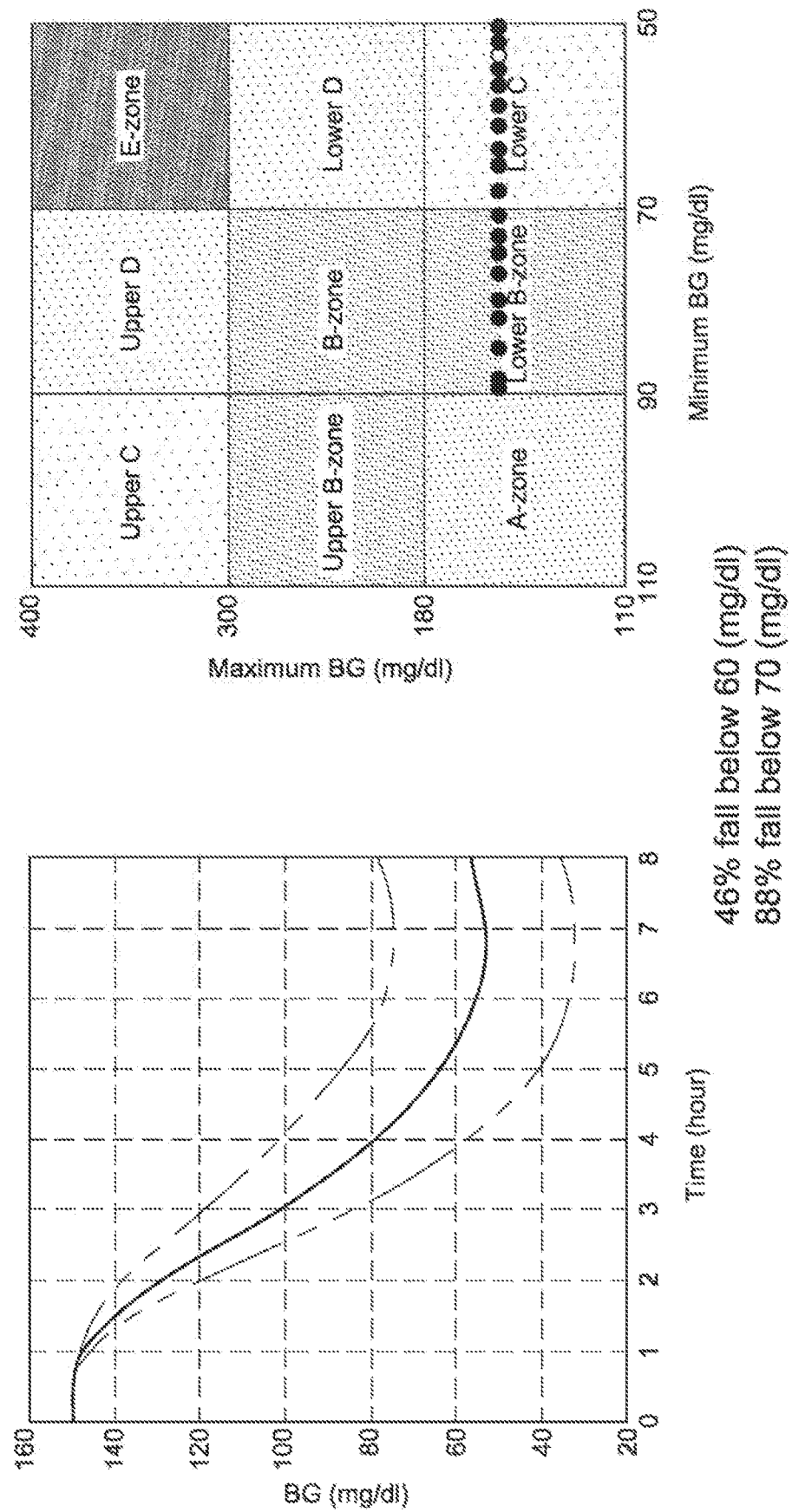
FIGS. 6A and 6B schematically provides simulation results from an exemplary embodiment of the CGM-based prevention of hypoglycemia system (CPHS).

FIG. 6(A) involves 100 in silico patients with T1DM, using the UVA and U. Padova Metabolic Simulator. All 100 patients start at time t=0 with a glucose concentration of 150 mg/dl and are subjected at that time to an elevated basal rate $J_{command}(t)$ that is two times what would be required to achieve a fasting blood glucose of 112.5 mg/dl. The experiment is designed to reflect the situation where a patient's insulin sensitivity is greatly enhanced, say due exercise. Note that 46% of the patients experience blood glucose below 60 (mg/dl), and 88% of the patients experience blood glucose below 70 (mg/dl). The chart demonstrates the minimum and maximum BG over the duration of the experiment plotted on the on the X- and Y-axis, respectively, and the graph indicates the BG (mg/dl) over time (hours).

Figure 6B:
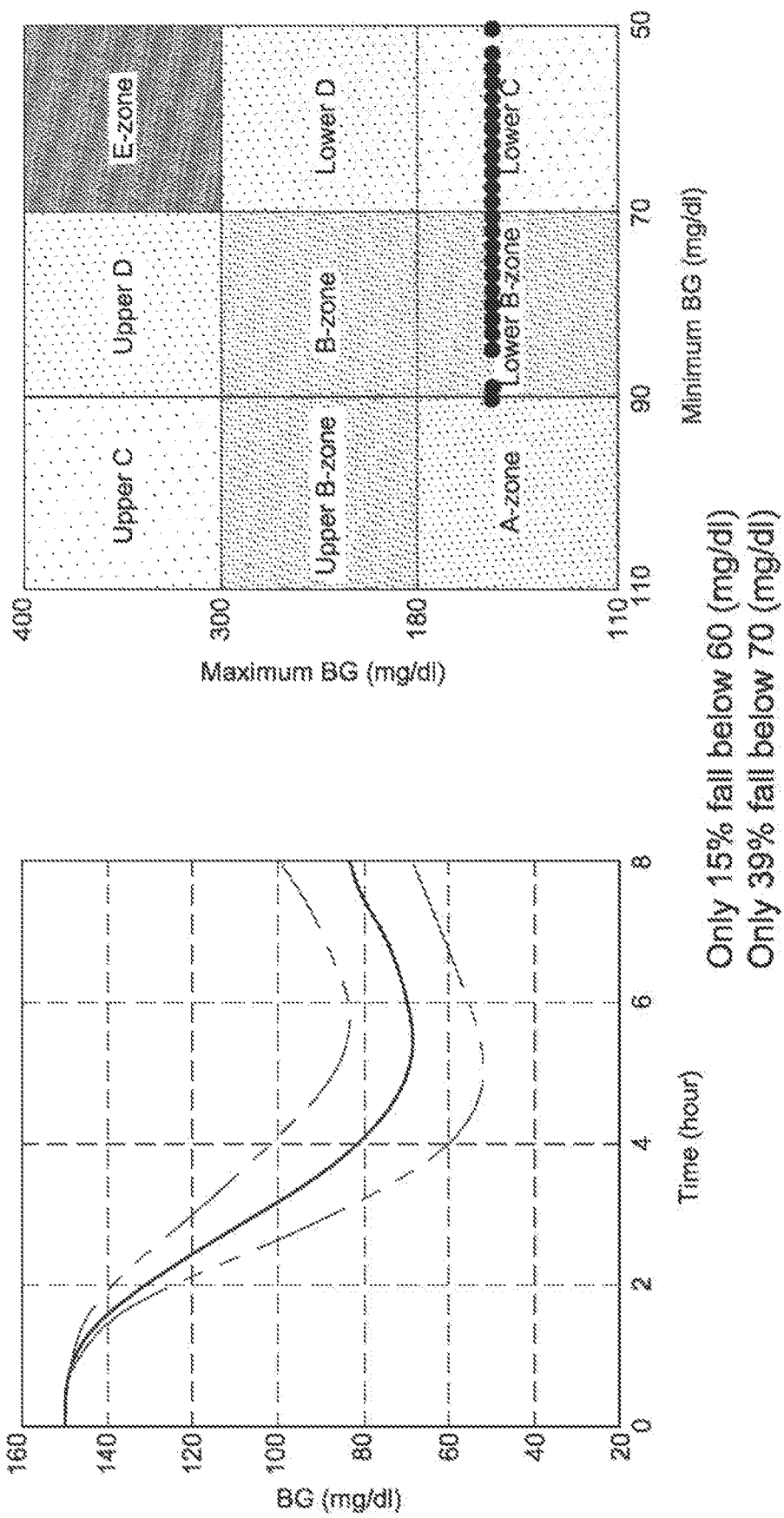
Figure 7A:
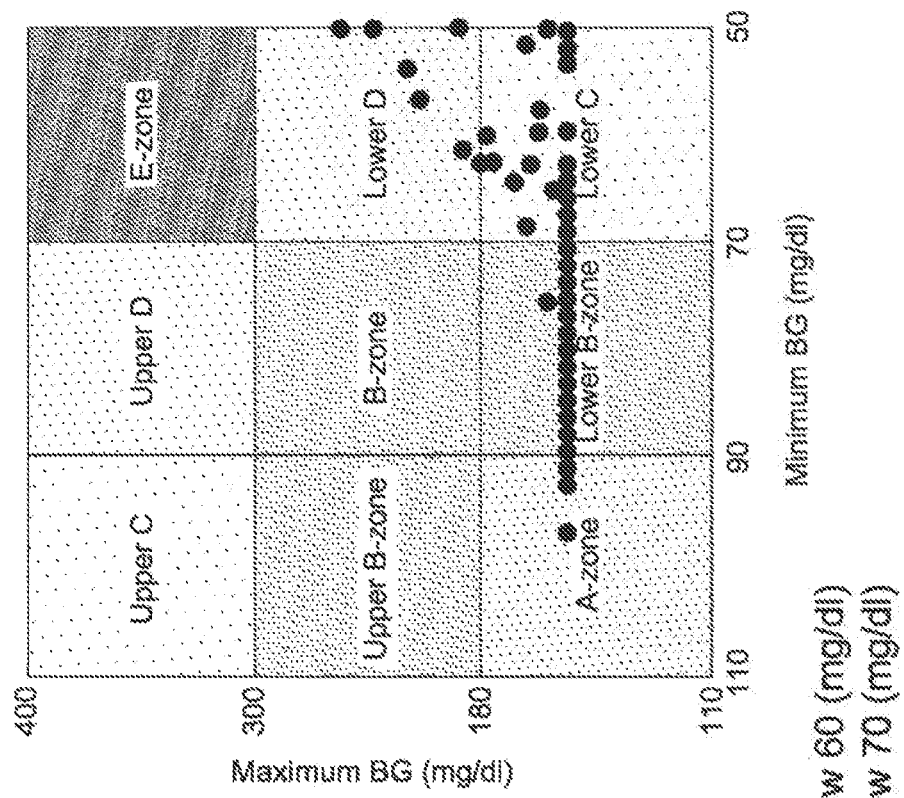
FIGS. 7A and 7B schematically provides simulation results from an exemplary embodiment of the CGM-based prevention of hypoglycemia system (CPHS).
Figure 7A:
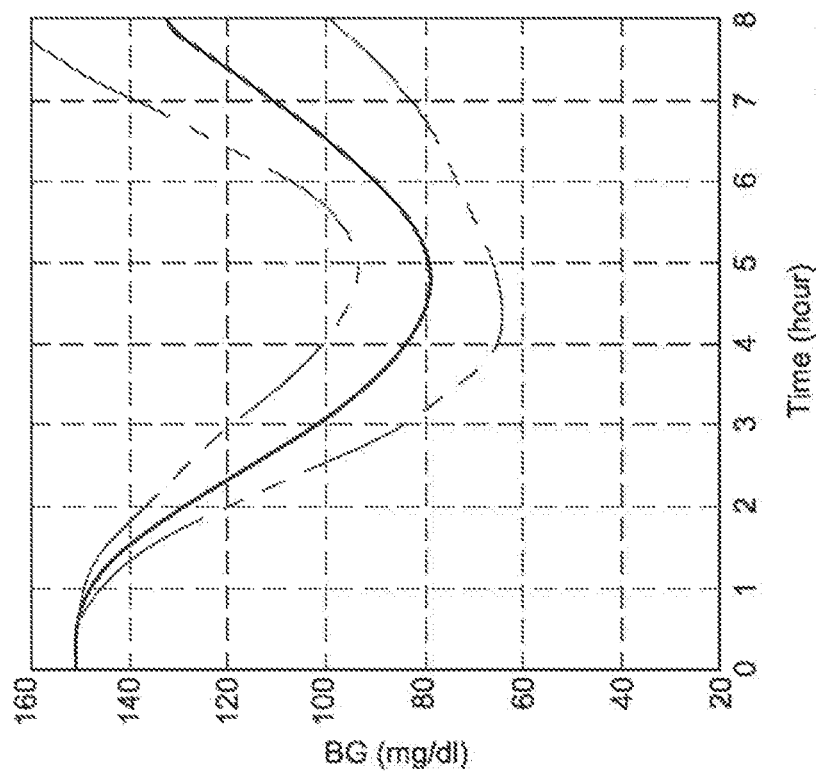
Figure 7B:
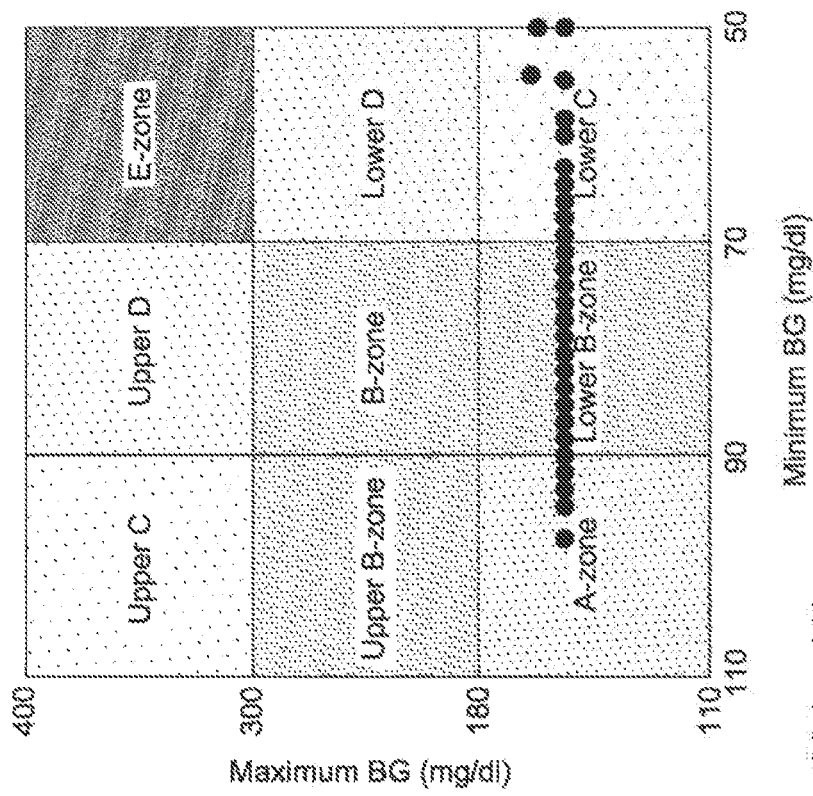
Figure 7B:
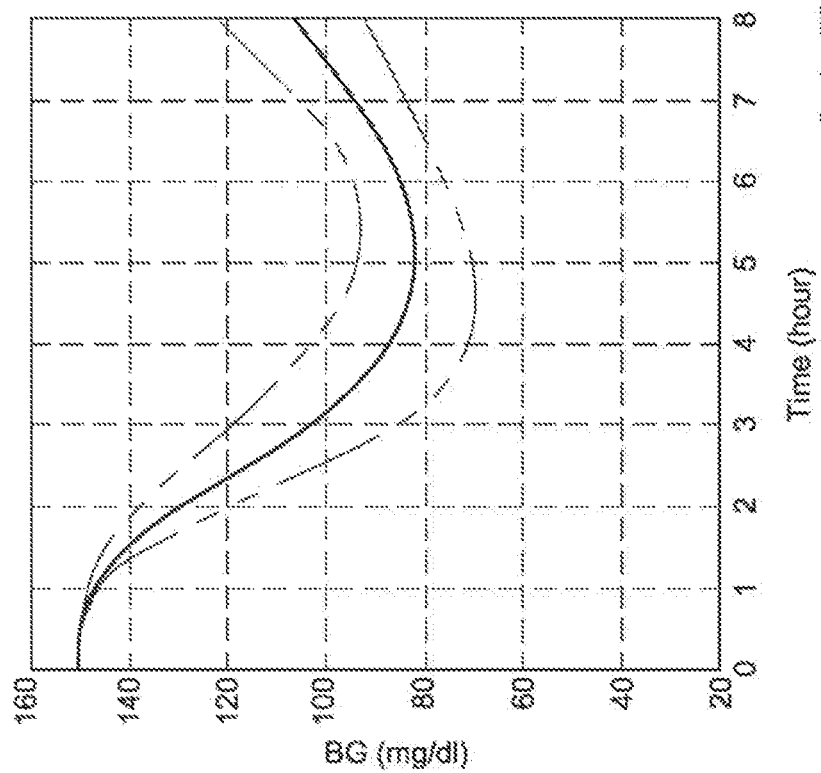

FIG. 6(B) presents the simulation with an elevated basal rate with CGM-only brakes. Here, for the 2× basal rate scenario, CGM-only brakes with k=1, M=1, and $\theta$=120 (mg/dl) substantially reduces the occurrence of hypoglycemia, with only 15% experiencing hypoglycemia below 60

(mg/dl), and only 39% of the population experiencing a blood glucose of 70 (mg/dl). The chart demonstrates the minimum and maximum BG over the duration of the experiment plotted on the on the X- and Y-axis, respectively, and the graph indicates the BG (mg/dl) over time (hours).

As a complement to the attenuation function of the system above, the CPHS (and related method and computer program product) employs a new hypoglycemia alarm that provides a color-coded signal to the patient based on the abstraction of a traffic light. In essence an embodiment of this system and related method will present a:

1. Green light to the patient whenever there is no risk of hypoglycemia;
2. Yellow light to the patient whenever there is a risk of hypoglycemia but hypoglycemia is not imminent and could be handled by insulin attenuation; and
3. Red light to the patient whenever hypoglycemia is inevitable regardless of the attenuation of the insulin pump.

In the CGM-only version of the alarm system, the method for determining which signal to present is as follows:

1. $R(t)=0$ presents a green light;
2. $R(t)>0$ and $y(t) \geq K_{red}$ presents a yellow light; and
3. $y(t) > K_{red}$ presents a red light.

The choice of the parameter $K_{red}$ also depends upon the embodiment of the system. If 60 mg/dl is acknowledged as the onset of hypoglycemia, then $K_{red}$ could be chosen as 65 mg/dl, so that the patient has the opportunity to administer rescue carbohydrates before the hypoglycemic threshold is crossed. To avoid false alarms, it might be desirable as an alternative to require $y(t) < K_{red}$ for a specified amount of time (e.g. two minutes) before tripping the red light.

Figure 5:
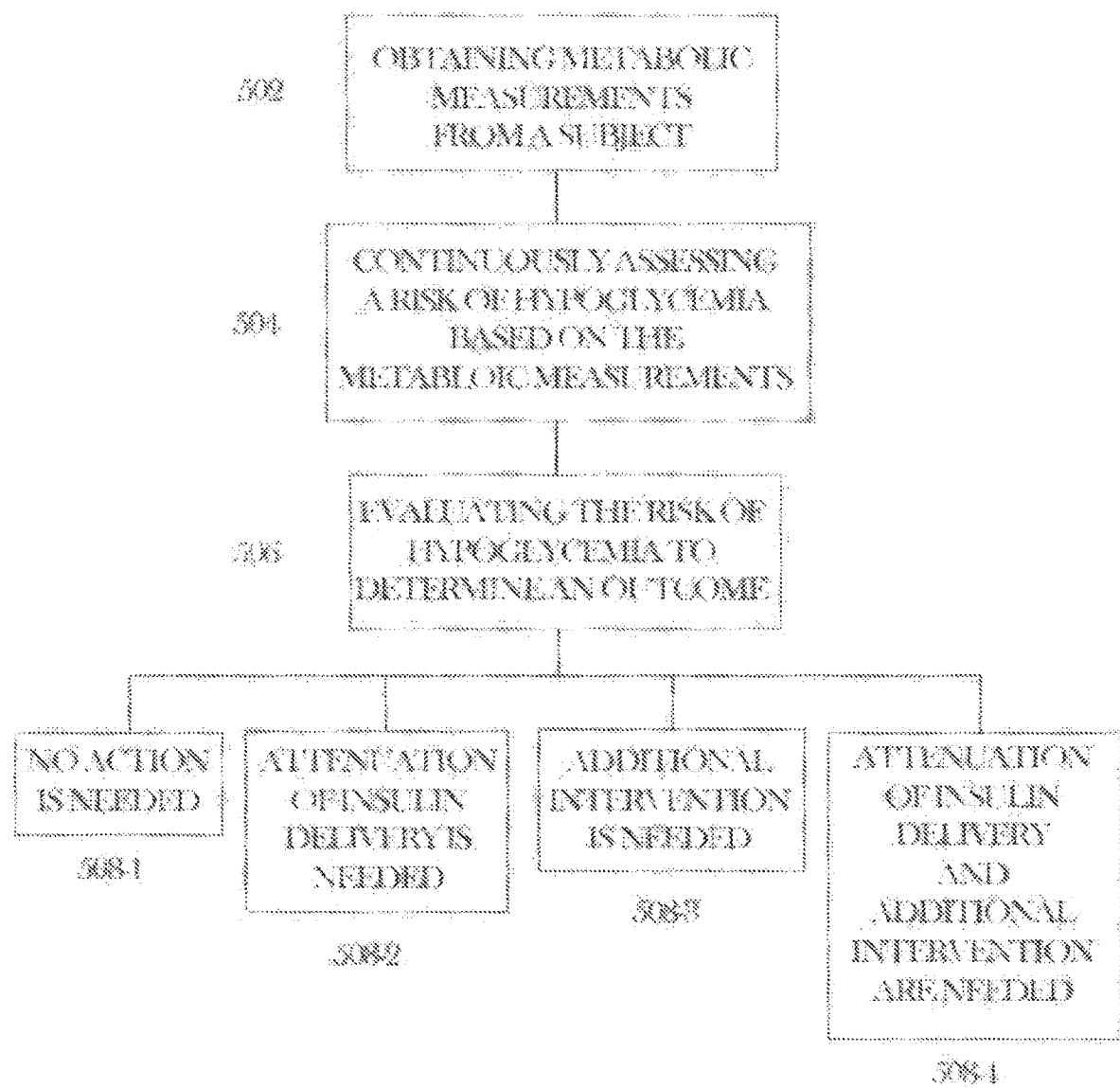
FIG. 5 schematically provides an exemplary embodiment of the CGM-based prevention of hypoglycemia method (and modules of a related system).

FIG. 5 illustrates an exemplary embodiment of the CGM-based prevention of hypoglycemia method and system. In an approach, in step 502 (or the applicable system module or means) obtains metabolic measurements from the subject. Based on the metabolic measurements, step 504 (or the applicable system module or means) includes continuously assessing the risk of hypoglycemia. Depending on the assessed risk of hypoglycemia, step 506 (or the applicable system module or means) includes evaluating the risk of hypoglycemia to determines what possible action to take. Possible actions (or their applicable system modules or means) may include step 508-1, taking no action; step 508-2, attenuating insulin delivery; step 508-3, taking additional intervention; and step 508-4, attenuating insulin delivery and taking additional intervention.

CPHS With CGM and Insulin Pump Data

Figure 4:
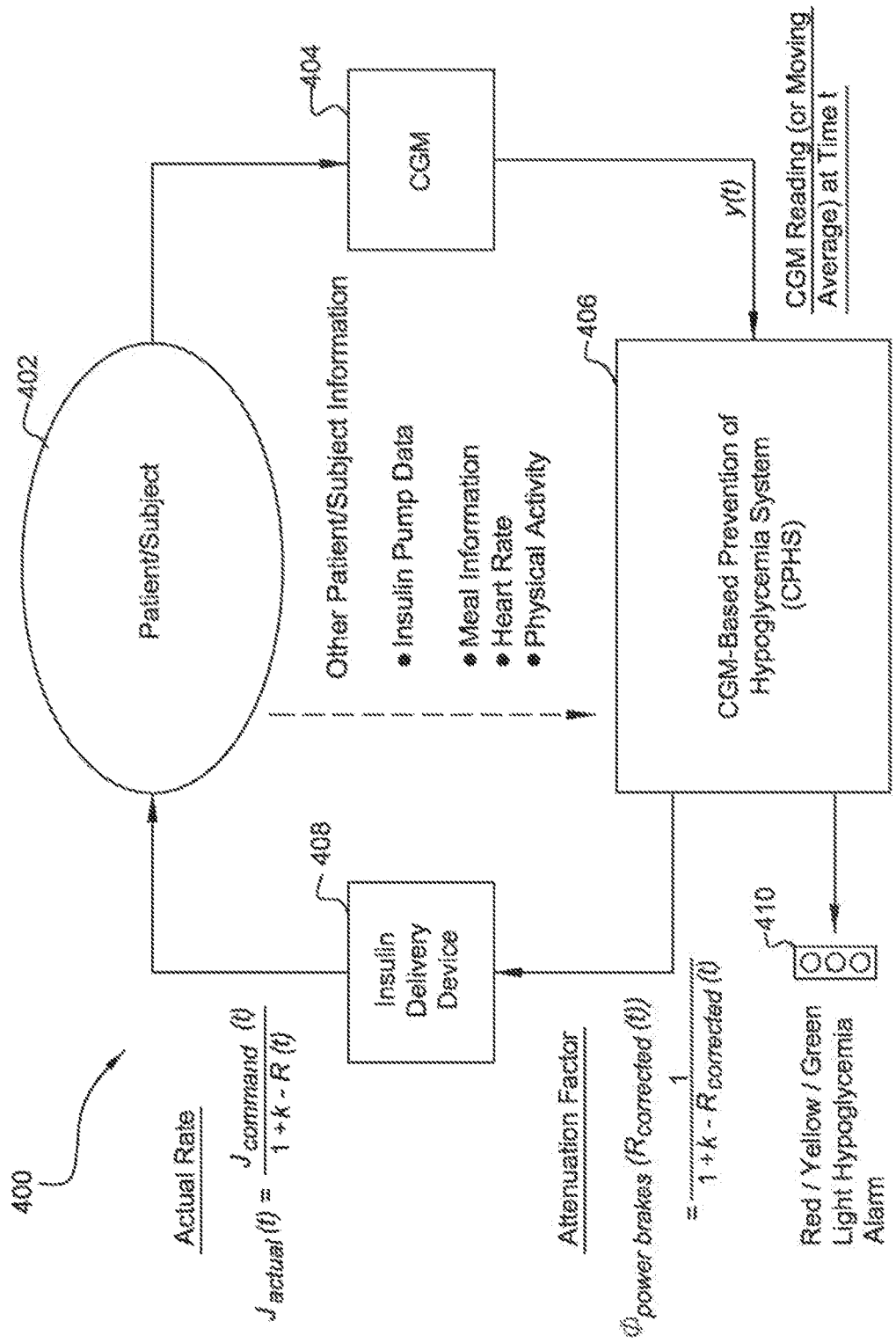
FIG. 4 schematically provides an exemplary embodiment of the CGM-based prevention of hypoglycemia system (CPHS).

This section describes the CPHS for the case where, in addition to CGM data, the system receives external data, including insulin pump data. Insulin pump data refers either to (1) commands from the user (in conventional therapy) or controller (in open- or closed-loop control) or (2) feedback from the pump regarding delivered insulin (regardless of the type of control employed). The method described here also extends to configurations where, in addition to CGM and insulin pump data, yet other inputs are available to the CPHS, including meal information, indications of physical activity, and heart rate information. The insulin pump data or other external input data are indirect metabolic measurements. These measurements are not collected directly from the patient and are collected from other sources that can indicate information about the current patient state. For instance, insulin pump data is an indirect metabolic measurement. It should be appreciated that an embodiment of the CPHS disclosed can take as inputs both direct metabolic measurements and indirect metabolic measurements. This general situation is depicted in FIG. 4. As before, the outputs of the system 400 are: (1) an attenuation factor designed to restrict the delivery of insulin when there is significant risk of hypoglycemia and (2) a red/yellow/green light alarm system to inform the user of impending hypoglycemia.

FIG. 4 presents an illustration of an enhanced hypoglycemia prevention system 400 including a CPHS, which uses CGM data and insulin pump data (associated with either conventional therapy or open or closed loop control systems) to (1) compute an attenuation factor based on an assessment of the risk of hypoglycemia and/or (2) present to the user red, yellow, or green lights indicating the risk of hypoglycemia. The subject or patient, 402, is a diabetic subject and the CGM 404 collects information about the patient. The CPHS 406 takes as input the blood glucose data acquired by the CGM 404. Based on this data, the CPHS 406 evaluates the risk of hypoglycemia and determines whether and what kind of action to take. These actions include taking no action, attenuating insulin delivery, and/or taking additional intervention. Depending on the risk of hypoglycemia, the visual indicator 410, displays a colored light (or other indicator as desired or required). As in the previous embodiments, if there is no risk of hypoglycemia, the CPHS 406 will take no action and the visual indicator 410 will present a green light. If the risk of hypoglycemia is low the CPHS 406 will attenuate insulin delivery, and the visual indicator 410 will present a yellow light. If the risk of hypoglycemia is high, the CPHS 406, will either (1) call for additional intervention, or (2) call for additional intervention and attenuate insulin delivery. In either case, the visual indicator 410 will present a red light.

When the CPHS (and related method and computer program product) has access to other data in addition to CGM data, an embodiment of the invention can correct the glucose signal used in the risk calculation. Here, the focus is on the case where, in addition to CGM data and possibly other signals, the CPHS has explicit access to insulin pump data coming either in the form of (1) user inputs (i.e. commanded insulin rate at any time and insulin boluses whenever they occur) or (2) feedback from the pump regarding delivered insulin. The system is generic in that requests for insulin may come either from conventional therapy (with the patient in charge) or from open- or closed-loop control. With the additional input data it is possible to compute a corrected glucose concentration $y_{corrected}(t)$ (mg/dl); two methods of computing $y_{corrected}(t)$ are described in the paragraphs that follow. The corrected glucose reading $y_{corrected}(t)$ is used to compute a corrected raw assessment of the risk of hypoglycemia $\tilde{R}_{corrected}(t)$, as below:

$$\tilde{R}_{corrected}(t) = \begin{cases} 10 \cdot [\gamma(\theta) \cdot (\ln(y_{corrected}(t))^{\alpha(\theta)} - \beta(\theta))]^2 & \text{if } 20 < y_{corrected}(t) < \theta \\ 100 & \text{if } y_{corrected}(t) \leq 20 \\ 0 & \text{otherwise.} \end{cases}$$

where, as before, the parameters $\alpha(\theta)$, $\beta(\theta)$, and $\gamma(\theta)$ are computed in advanced based on a threshold glucose concentration $\theta$ (mg/dl), which is specific to the embodiment of the CPHS. Note that $\theta$ is the glucose concentration below which the risk function will be positive. Values for $\alpha(\theta)$, $\beta(\theta)$, and $\gamma(\theta)$ are listed for different thresholds $\theta$ in Table 1. Finally, the corrected risk assessment $R_{corrected}(t)$ (not raw) is computed as $$R_{corrected}(t) = \frac{1}{M}\sum_{\tau=0}^{M-1} \tilde{R}_{corrected}(t-\tau)$$

where, as before, M is the size of the moving average window for risk assessment.

The corrected assessment of risk $R_{corrected}(t)$ is used to compute a power brakes pump attenuation factor $\phi_{powerbrakes}$ ($R_{corrected}(t)$), as follows:

$$\phi_{powerbrakes}(R_{corrected}(t)) = \frac{1}{1 + k \cdot R_{corrected}(t)}$$

where k is an aggressiveness parameter that may be adjusted to match the patient's physiology (i.e. according to the patient's insulin sensitivity). As illustrated in FIG. 4, the attenuation factor would be used by the insulin delivery device to compute reduced actual pump rate $J_{actual}(t)$ (U/hr) according to:

$$J_{actual}(t) = \phi_{powerbrakes}(R_{corrected}(t)) \cdot J_{command}(t)$$

where $J_{command}(t)$ is the rate of insulin injection (U/hr) that the pump is set to administer, $J_{actual}(t)$ is the attenuated insulin rate (U/hr). Thus, as with the brakes, the power brakes algorithm is designed to smoothly adjust insulin rate commands to the insulin pump to avoid hypoglycemia.

As with the CGM-only brakes, the aggressiveness parameter in some embodiments will be set as k=1, M=1, and the threshold θ will be set to the nominal value of 112.5 (mg/dl). In other embodiments, the parameters k, M, and θ will be manually set to other fixed values in concert with the patient's physician (e.g. according to the patient's insulin sensitivity and eating behavior) or input by the patient or other individual providing the input.

In yet other embodiments, the parameters k, M, and θ will be set according to regression formulas involving the patient's physical characteristics (e.g. body weight, total daily insulin TDI (U), carbohydrate ratio, correction factor CF (mg/dl/U), age, etc.). One such regression formula for k follows:

$$k = \exp(-0.7672 - 0.0091 \cdot TDI + 0.0449 \cdot CF).$$

Experiments run on the FDA-accepted T1DM simulator at the University of Virginia show that the performance of the brakes varies smoothly as a function of k, M, and θ, and, while setting these parameters optimally leads to the best ability to prevent hypoglycemia, adverse events do not arise when non-optimal values are chosen.

Two methods are disclosed for computing a corrected glucose level. The first method of computing corrected glucose involves the use of a metabolic state observer, which in turn (1) requires a model of blood glucose-insulin dynamics and (2) requires knowledge of insulin pump commands and ingested carbohydrates. x(t) denotes a vector of metabolic states associated with the patient, representing things like interstitial glucose concentration, plasma glucose concentration, insulin concentrations, contents of the gut, etc. x̂(t) denotes the estimate of x(t) using all available input data up to time t, based on a linear state space model expressed generically as $$x(t) = Ax(t-1) + Bu(t-1) + Gw(t-1),$$

where u(t) represents insulin inputs into the body and w(t) represents ingested carbohydrates. The corrected glucose reading is computed according to, $$y_{corrected}(t) = C\hat{x}_\tau(t),$$

where C is a matrix that relates the metabolic state vector to measured glucose, t is a nonnegative integer parameter, and $$\hat{x}_\tau(t) = A^\tau \hat{x}(t) + A(\tau)Bu(t) + A(\tau)Gw(t)$$

where $A^\tau$ is the A matrix of the state space model raised to the r-th power and $$A(\tau) = \begin{cases} 0 & \text{if } \tau = 0 \\ \sum_{s=0}^{\tau-1} A^s & \text{if } \tau > 0. \end{cases}$$

In this method of computing $y_{corrected}(t)$, the state space model (A,B,G,C), the state observer giving the estimate x̂(t), and the parameter τ are all specific to the embodiment of the invention.

The choice of t depends upon the embodiment of the system. τ=0 corresponds to assessing risk based on the best estimate of blood glucose based on all of the data received up to time t. τ>0 corresponds to an assessment of the future risk of hypoglycemia, giving power brakes the opportunity to intervene well before the onset of hypoglycemia, improving the chance that hypoglycemia can be avoided. An important benefit of an embodiment of the power brakes is that as soon as anticipated blood glucose reaches 110 mg/dl the attenuation-affect is release (sooner than would be the case with just brakes). In some embodiments, τ can be allowed to vary. For example, if the patient is unwilling unable to provide detailed information about meal content (making it difficult to predict future blood sugar), it may be desirable to adjust τ in the time frame after meals, as follows:

$$\tau = \begin{cases} 0, & \text{if } t - t_{meal} < 60, \\ 30, & \text{otherwise}, \end{cases}$$

where $t_{meal}$ represents the time of the most recent meal.

The second method of computing $y_{corrected}(t)$ involves the use of the patient's correction factor CF (used in computing appropriate correction boluses in conventional therapy) and requires knowledge of the amount of active correction insulin $i_{correction}(t)$ (U) in the patient's body at time t, which can be obtained from standard methods of computing insulin on board. The formula for $y_{corrected}(t)$ in this case is $$y_{corrected}(t) = \alpha \cdot (y(t) - CF \cdot i_{correction}(t)) + (1-\alpha) \cdot y(t)$$

where α is an embodiment-specific parameter chosen in the unit interval [0, 1] and y(t) is the most recent CGM sample (or moving average of recent CGM samples).

Testing was completed to determine the viability of this embodiment of the invention. The following results show the efficacy of the power brakes algorithm, technique and methodology using the first method of computing corrected glucose for $y_{corrected}(t)$. A population-average model was used for glucose-insulin kinetics, as described by the vector difference equation:

$$x(t) = Ax(t-1) + Bu(t-1) + G\omega(t-1)$$

where t is a discrete time index with the interval from t to t+1 corresponding to one minute of real time and
1. x(t)=(∂G(t) ∂X(t) ∂$I_{sc1}$(t) ∂$I_{sc2}$(t) ∂$I_p$(t) ∂$G_{sc}$(t) ∂$Q_1$(t) ∂$Q_2$(t))$^T$ is a vector of state variables referring to:
   a. blood glucose: ∂G(t)=G(t)−$G_{ref}$, where G(t) mg/dl is blood glucose concentration at minute t and $G_{ref}$=112.5 (mg/dl) is a reference value for blood glucose;

b. remote compartment insulin action: $\partial X(t) = X(t) - X_{ref}$, where $X(t)$ (min$^{-1}$) represents the action of insulin in the remote compartment and $X=0$(min$^{-1}$) is a reference value;

c. interstitial insulin, first compartment: $\partial I_{sc1}(t) = I_{sc1}(t) - I_{sc1,ref}$, where $I_{sc1}(t)$ (mU) is insulin stored in the first of two interstitial compartments and $I_{sc1,ref} = 1.2949 \times 10^3$ (mU) is a reference value;

d. interstitial insulin, second compartment: $\partial I_{sc2}(t) = I_{sc2}(t) - I_{sc2,ref}$, where $I_{sc2}(t)$ (mU) is insulin stored in the first of two interstitial compartments and $I_{sc2,ref} = 1.2949 \times 10^3$ (mU) is a reference value;

e. plasma insulin: $\partial I_p(t) = I_p(t) - I_{p,ref}$, where $I_p(t)$ (mU) is plasma insulin and $I_{p,ref} = 111.2009$ (mU) is a reference value;

f. interstitial glucose concentration: $\partial G_{sc}(t) = G_{sc}(t) - G_{sc,ref}$, where $G_{sc}(t)$ (mg/dl) is the concentration of glucose in interstitial fluids, and $G_{sc,ref} = 112.5$ (mg/dl) is a reference value;

g. gut compartment 1: $\partial Q_1(t) = Q_1(t) - Q_{1,ref}$, where $Q_1(t)$ (mg) is glucose stored in the first of two gut compartments and $Q_{1,ref} = 0$ (mg) is a reference value; and h. gut compartment 2: $\partial Q_2(t) = Q_2(t) - Q_{2,ref}$, where $Q_2(t)$ (mg) is glucose stored in the first of two gut compartments and $Q_{2,ref} = 0$ (mg) is a reference value.

2. $u(t) = J_{command}(t) - J_{basal}(t)$ (mU/min) is the insulin differential control signal at time t, where $J_{command}(t)$ (mU/min) is the current rate of insulin infusion and $J_{basal}(t)$ (mU/min) is the patient's normal/average basal rate at time t.

3. $\omega(t) = meal(t) - meal_{ref}$ (mg/min) is the ingested glucose disturbance signal at time t, where $meal(t)$ is the rate of glucose ingestion and $meal_{ref} = 0$ (mg/min) is a reference meal input value.

4. the state space matrices A, B, and G are $$A = \begin{bmatrix} .9913 & -102.7 & 1.50 \times 10^{-8} & -2.89 \times 10^{-6} & -4.1 \times 10^{-4} & 0 & 2.01 \times 10^{-6} & 4.30 \times 10^{-5} \\ 0 & .839 & 5.23 \times 10^{-10} & 7.44 \times 10^{-8} & 6.84 \times 10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9 \times 10^{-4} & .0180 & .7882 & 0 & 0 & 0 \\ .0865 & -4.667 & -2.73 \times 10^{-10} & -6.59 \times 10^{-8} & -1.26 \times 10^{-5} & .9131 & 6.00 \times 10^{-8} & 1.90 \times 10^{-6} \\ 0 & 0 & 0 & 0 & 0 & 0 & .9083 & 0 \\ 0 & 0 & 0 & 0 & 0 & 0 & .09115 & .9891 \end{bmatrix}$$

$$B^T = [-3.05 \times 10^{-9} \quad 1.34 \times 10^{-10} \quad .9900 \quad .0100 \quad 6.50 \times 10^{-5} \quad -4.61 \times 10^{-11} \quad 0 \quad 0]$$

$$G^T = [6.76 \times 10^{-7} \quad 0 \quad 0 \quad 0 \quad 0 \quad 1.52 \times 10^{-8} \quad .9534 \quad 0.0464]$$

Estimates $\hat{x}(t)$ of $x(t)$ are computed based on knowledge of infused insulin $u(t)$ and CGM measurements $y(t)$(mg/dl). The measurement signal can be modeled as follows:

$$y(t) - G_{ref} = Cx(t) + v(t)$$

where $v(t)$ (mg/dl) represents CGM signal noise and the state space matrix C is $$C^T = [1 \, 0 \, 0 \, 0 \, 0 \, 0 \, 0 \, 0]$$

The metabolic state observer is derived from the state space model for $x(t)$ and $y(t)$ as a Kalman filter, treating the meal disturbance process $w(t)$ and the noise process $v(t)$ as zero-mean, white, Gaussian processes with covariances $R = k_1 = 0.01$ and $Q = k_2 = 0.00001$ respectively. Even though meals $w(t)$ and sensor noise $v(t)$ are not zero-mean, white, Guassian processes in reality, the resulting Kalman filter is still a stable state observer.

Some T1DM patients or subjects experience highly variable insulin sensitivity (e.g. after physical activity). For such a patient, it can happen that his/her basal rate of insulin delivery, which is tuned to achieve fasting euglycemia under normal circumstances, is occasionally suddenly too high, putting the patient at risk of hypoglycemia. For these patients, the power brakes with $k=1$ and $\theta=120$ (mg/dl) will successfully mitigate the risk of hypoglycemia, as illustrated in the simulation results of FIG. 7.

Turning to FIG. 7, as in FIG. 6, this simulation experiment involves 100 in silico patients with T1DM, using the UVA and U. Padova Metabolic Simulator. All 100 patients start at time $t=0$ with a glucose concentration of 150 mg/dl and are subjected at that time to an elevated basal rate $J_{command}(t)$ that is two times what would be required to achieve a fasting blood glucose of 112.5 mg/dl. Recall from FIG. 6 that 46% of the patients experience blood glucose below 60 (mg/dl), and 88% of the patients experience blood glucose below 70 (mg/dl). FIG. 7(A) illustrates an elevated basal scenario using power brakes with $k=1$, $M=1$, $\theta=120$ (mg/dl), and $\tau=0$ (minutes). The chart demonstrates the minimum and maximum BG over the duration of the experiment plotted on the on the X- and Y-axis, respectively, and the graph indicates the BG (mg/dl) over time (hours). In this case, the power brakes compute the risk assessment using just the current best estimate of the patient's blood glucose (i.e. $\tau=0$) based on all available information. Note that only 12% of the patients experience blood glucose below 60 mg/dl and only 33% of the patients experience blood glucose below 70 (mg/dl). FIG. 7(B) illustrates an elevated basal scenario using power brakes with $k=1$, $\theta=120$ (mg/dl), and $\tau=30$ (minutes). Here, for the 2× basal rate scenario, CGM-only brakes with $k=1$, $M=1$, $\theta=120$ (mg/dl) substantially reduce the occurrence of hypoglycemia, with 15% experiencing hypoglycemia below 60 (mg/dl), and only 39% of the population experiencing a blood glucose of 70 mg/dl. The chart demonstrates the minimum and maximum BG over the duration of the experiment plotted on the on the X- and Y-axis, respectively, and the graph indicates the BG (mg/dl) over time (hours).

Patients often administer pre-meal insulin boluses in anticipation of the meal that they are about to take. In unusual circumstances, the patient may forget or otherwise be unable to eat the anticipated meal, and, of course, this puts the patient at severe risk of hypoglycemia. For these patients, the power brakes can act to reduce basal insulin so as to substantially reduce the incidence of hypoglycemia, as illustrated in FIGS. 8 and 9.

Figure 8:
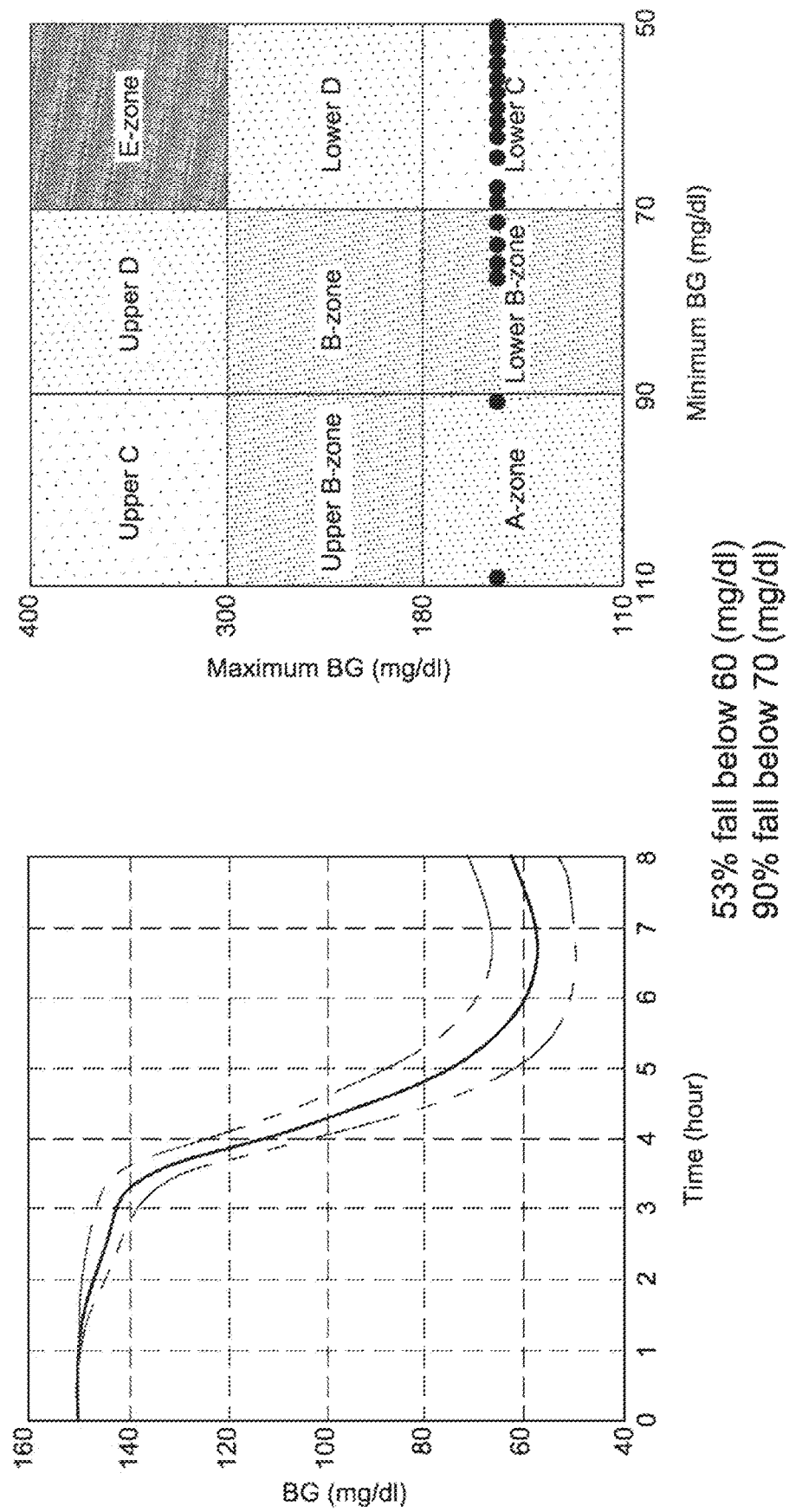
FIG. 8 schematically provides simulation results from an exemplary embodiment of the CGM-based prevention of hypoglycemia system (CPHS).

FIG. 8 is a simulation experiment involving 100 in silico patients with T1DM, using the UVA and U. Padova Metabolic Simulator. All 100 patients start at time $t=0$ with a glucose concentration of 150 mg/dl and are subjected a meal bolus at hour 3; all 100 patients skip the intended meal and hold their basal rate of insulin delivery $J_{command}(t)$ at what would be required to maintain a fasting blood glucose of 112.5 mg/dl. Note that because the carbohydrates of the meal never arrive, all patients experience a severe drop in blood glucose. 53% of the patients experience blood glucose below 60 (mg/dl); 90% experience blood glucose below 70 (mg/dl). The chart demonstrates the minimum and maximum BG over the duration of the experiment plotted on the on the X- and Y-axis, respectively, and the graph indicates the BG (mg/dl) over time (hours).

Figure 9A:
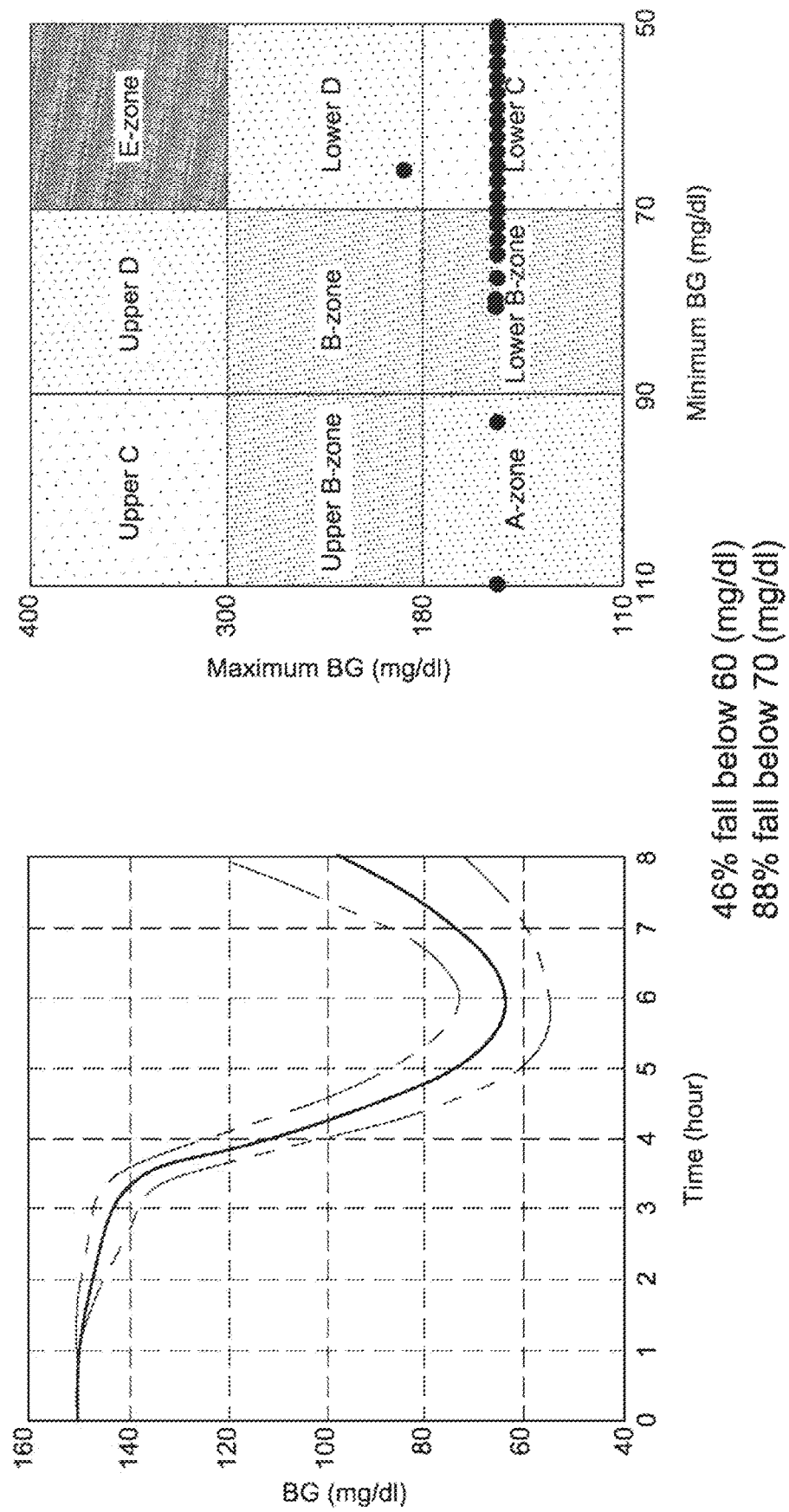
FIGS. 9A and 9B schematically provides simulation results from an exemplary embodiment of the CGM-based prevention of hypoglycemia system (CPHS).
Figure 9B:
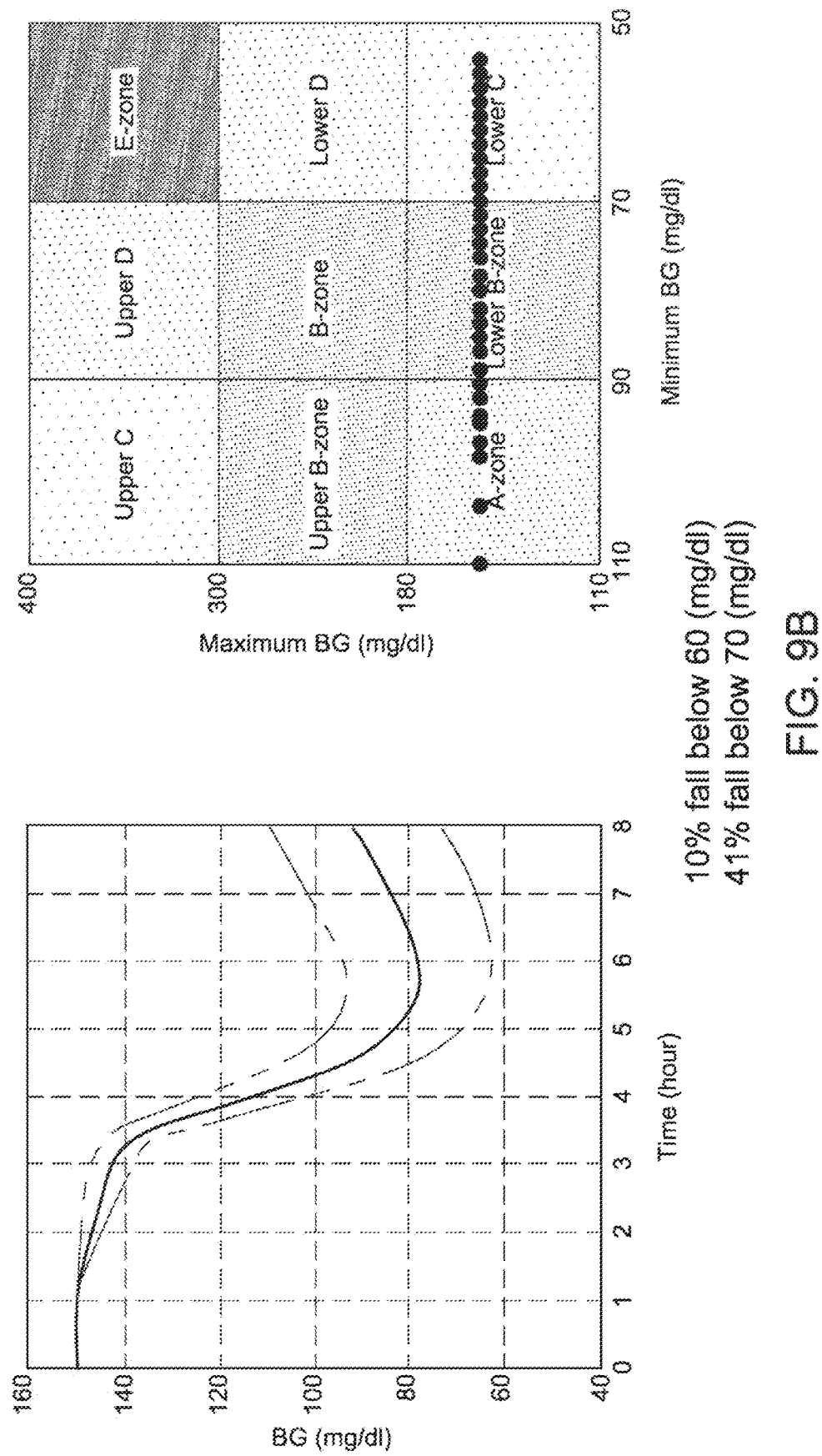

FIG. 9 is an illustration of an embodiment of the invention, implemented in the simulator. As in FIG. 8, all 100 patients start at time t=0 with a glucose concentration of 150 mg/dl and are subjected a meal bolus at hour 3; all 100 patients skip the intended meal and hold their basal rate of insulin delivery $J_{command}(t)$ at what would be required to maintain a fasting blood glucose of 112.5 mg/dl. FIG. 9(A) presents the power brakes embodiment with k=1, θ=120 (mg/dl), and τ=0 (minutes). With the power brakes (τ=0), 46% of the patients experience blood glucose below 60 (mg/dl); only 88% of the patients experience blood glucose below 70 (mg/dl). The chart demonstrates the minimum and maximum BG over the duration of the experiment plotted on the on the X- and Y-axis, respectively, and the graph indicates the BG (mg/dl) over time (hours). FIG. 9(B) presents the power brakes embodiment with k=1, M=1, and θ=120 (mg/dl), and t=30 (minutes). Here, the power brakes with τ=30 minutes, give a very substantial improvement in preventing hypoglycemia: only 10% of the patients experience blood glucose below 60 (mg/dl); only 41% of the patients experience blood glucose below 70 (mg/dl). The chart demonstrates the minimum and maximum BG over the duration of the experiment plotted on the on the X- and Y-axis, respectively, and the graph indicates the BG (mg/dl) over time (hours).

An embodiment of the CPHS (and related method and computer program product) with Insulin Input Commands, as illustrated in FIG. 4, uses a new hypoglycemia alarm system that provides a color-coded signal to the patient based on the abstraction of a traffic light, augmenting the hypoglycemia prevention capabilities of the power brakes themselves. In essence an embodiment of this system will present a:

1. Green light to the patient whenever there is no risk of hypoglycemia;
2. Yellow light to the patient whenever there is a risk of hypoglycemia but hypoglycemia is not imminent and could be handled by insulin attenuation; and
3. Red light to the patient whenever hypoglycemia is inevitable regardless of the attenuation of the insulin pump.

Having access to additional information (besides just CGM data), the Red/Yellow/Green Light Hypoglycemia Alarm System, uses the corrected measurement value $y_{corrected}(t)$ and the corrected risk function $R_{corrected}(t)$ as a principle means of determining what signal to present:

1. $R_{corrected}(t)=0$ presents a green light;
2. $R_{corrected}(t)>0$ and $y_{corrected,OFF}(t) \geq K_{red}$ presents a yellow light; and
3. $y_{corrected,OFF}(t) > K_{red}$ presents a red light, where $y_{corrected,OFF}(t)$ is an assessment of anticipated blood glucose concentration given that the insulin pump is completely shut down.

The choice of the parameter $K_{red}$ also depends upon the embodiment of the system. If 60 mg/dl is acknowledged as the onset of hypoglycemia, then $K_{red}$ could be chosen as 65 mg/dl, so that the patient has the opportunity to administer rescue carbohydrates before the hypoglycemic threshold is crossed. To avoid false alarms, it might be desirable as an alternative to require $BG_{off}(t+\sigma|t)<K_{red}$ for a specified amount of time (e.g. two minutes) before tripping the red light.

Building on the infrastructure for computing $y_{corrected}(t)$ in the power brakes, it is possible to compute $y_{corrected,OFF}(t)$ as $$y_{corrected,OFF}(t) = C\hat{x}_{\sigma,OFF}(t),$$

where σ is a nonnegative integer parameter, and $$\hat{x}_{\sigma,OFF}(t) = A^\sigma \hat{x}(t) + A(\tau)Bu_{OFF}(t) + A(\tau)Gw(t)$$

where $\hat{x}(t)$ is the current estimate of the patient's metabolic state and $u_{OFF}(t)$ is input signal corresponding to the insulin pump being completely shut down.

As with t in the computation of $y_{corrected}(t)$, the value of a is specific to the embodiment of the invention. Note that σ>0 corresponds to the anticipated value of blood glucose assuming that no more insulin is delivered.

A second method of computing $y_{corrected,OFF}(t)$ corresponds to second method of computing $y_{corrected}(t)$ described above. In this case, $$y_{corrected,OFF}(t) = y(t) \cdot CF \cdot i_{correction}(t)$$

where y(t) is the most recent CGM sample (or moving average of recent CGM samples) and CF and $i_{correction}(t)$ are as they were above.

An exemplary embodiment of the Red/Yellow/Green Light Hypoglycemia Alarm System is now presented. Relevant parameters are as follows:

1. Red Light Alarm Parameters: $K_{red}$=80 (mg/dl) and σ=15 (minutes);
2. Yellow Light Alarm Parameters: θ=112.5 (mg/dl), and τ=15 (minutes); and
3. No pump attenuation, so that even when R(t)>0 the actual rate of insulin infusion is equal to commanded insulin.

Figure 10:
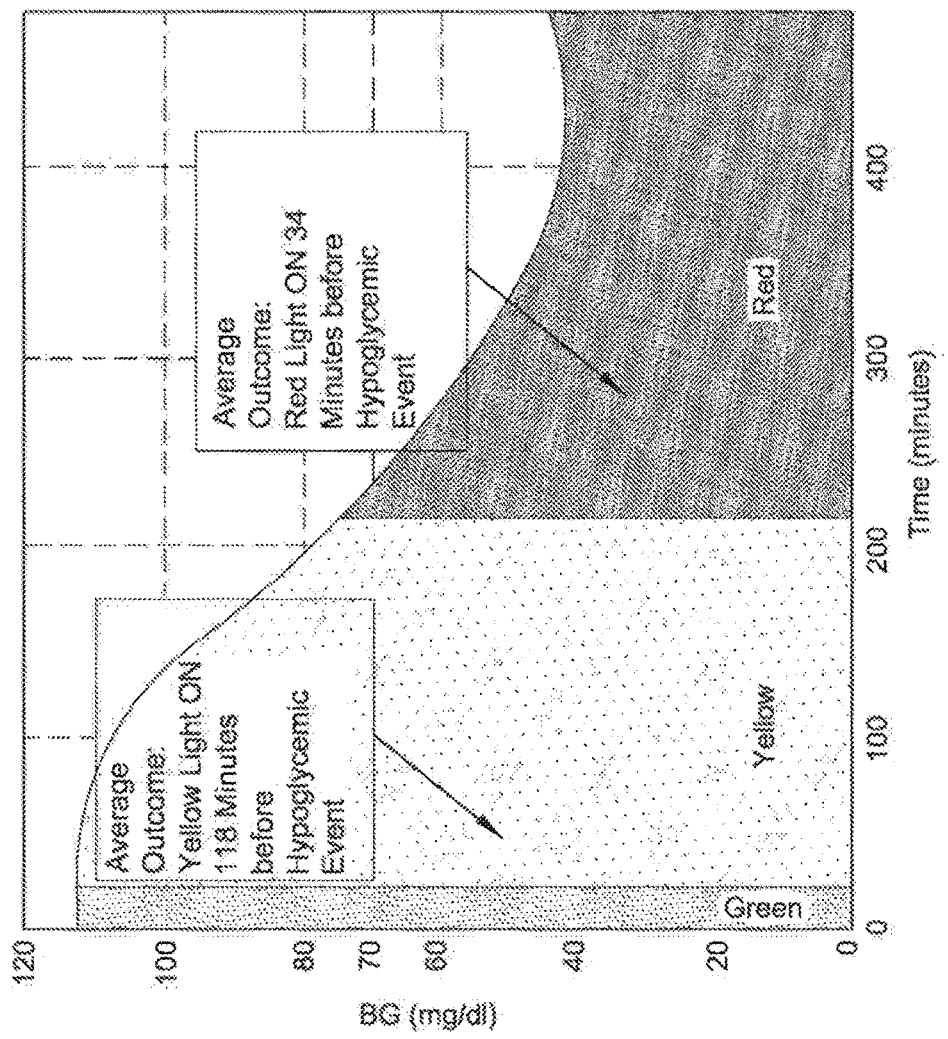
FIG. 10 schematically provides simulation results from an exemplary embodiment of the CGM-based prevention of hypoglycemia system (CPHS).

FIG. 10 shows results from the UVA/U. Padova Metabolic Simulator for 100 adult Type 1 in silico patients, with basal rates of insulin delivery set to be twice their fasting levels. With elevated basal rates, all 100 patients eventually become hypoglycemic (by crossing 60 (mg/dl)). Note that on average the yellow light turns on 118 minutes before hypoglycemia and the red light turns on 34 minutes before hypoglycemia. The plot shows the transition from green to yellow to red for a representative subject. The plot demonstrates BG, mg/dl, on the Y-axis and time, minutes, on the X-axis.

Figure 11:
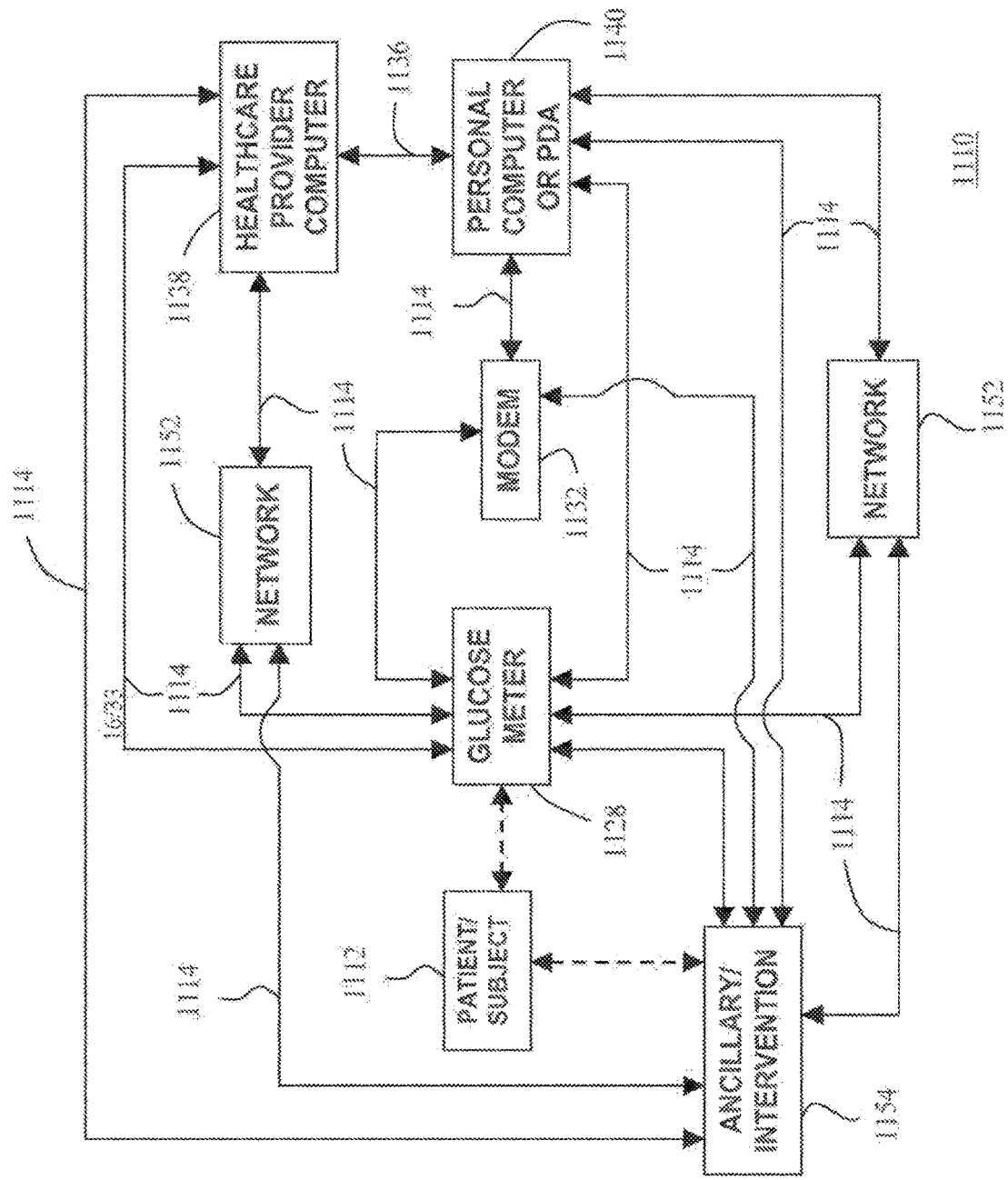
FIG. 11: provides a schematic block diagram of an aspect of an embodiment of the present invention relating processors, communications links, and systems, for example.
Figure 12:
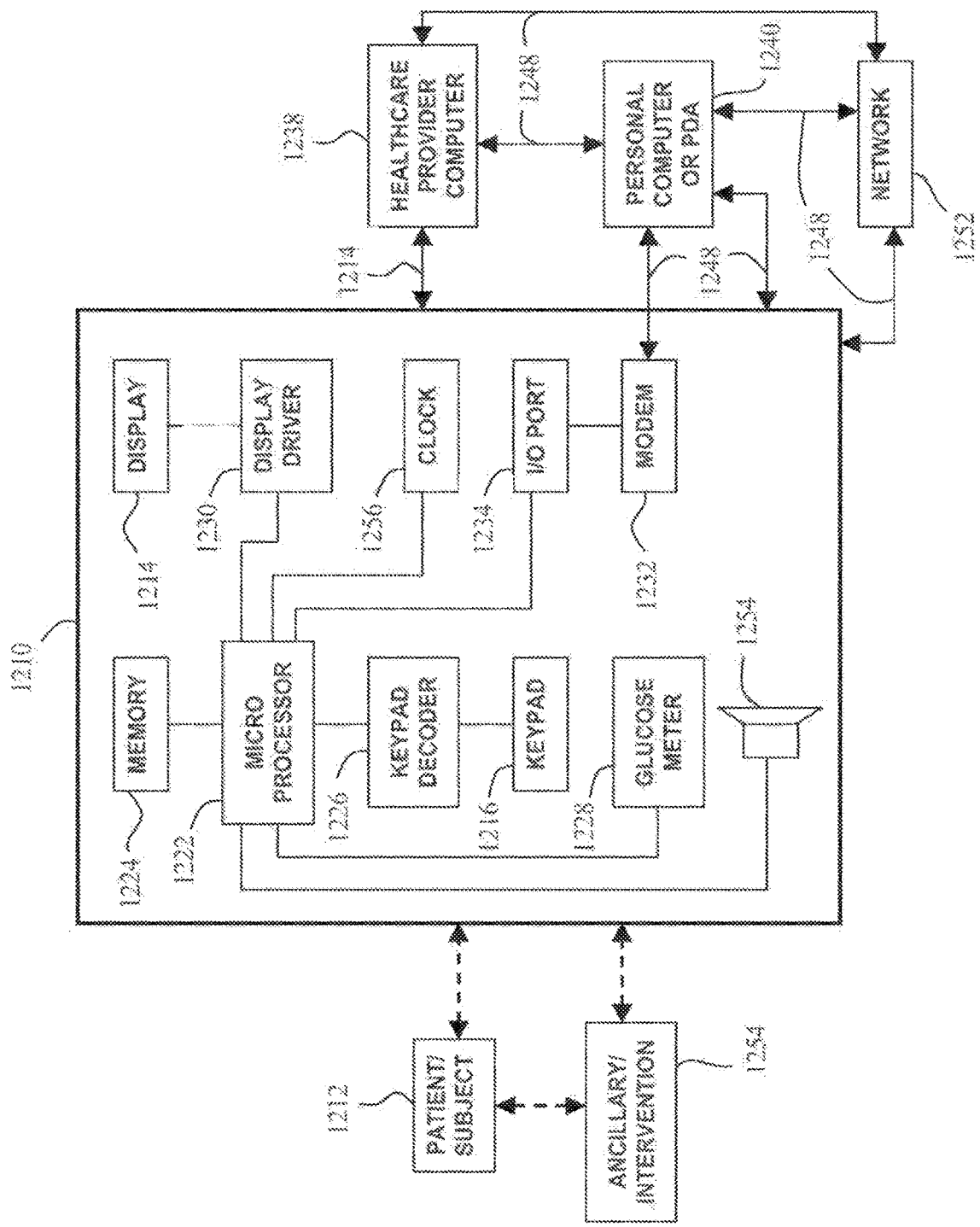
FIG. 12: Provides a schematic block diagram of an aspect of an embodiment of the present invention relating processors, communications links, and systems, for example.
Figure 13:
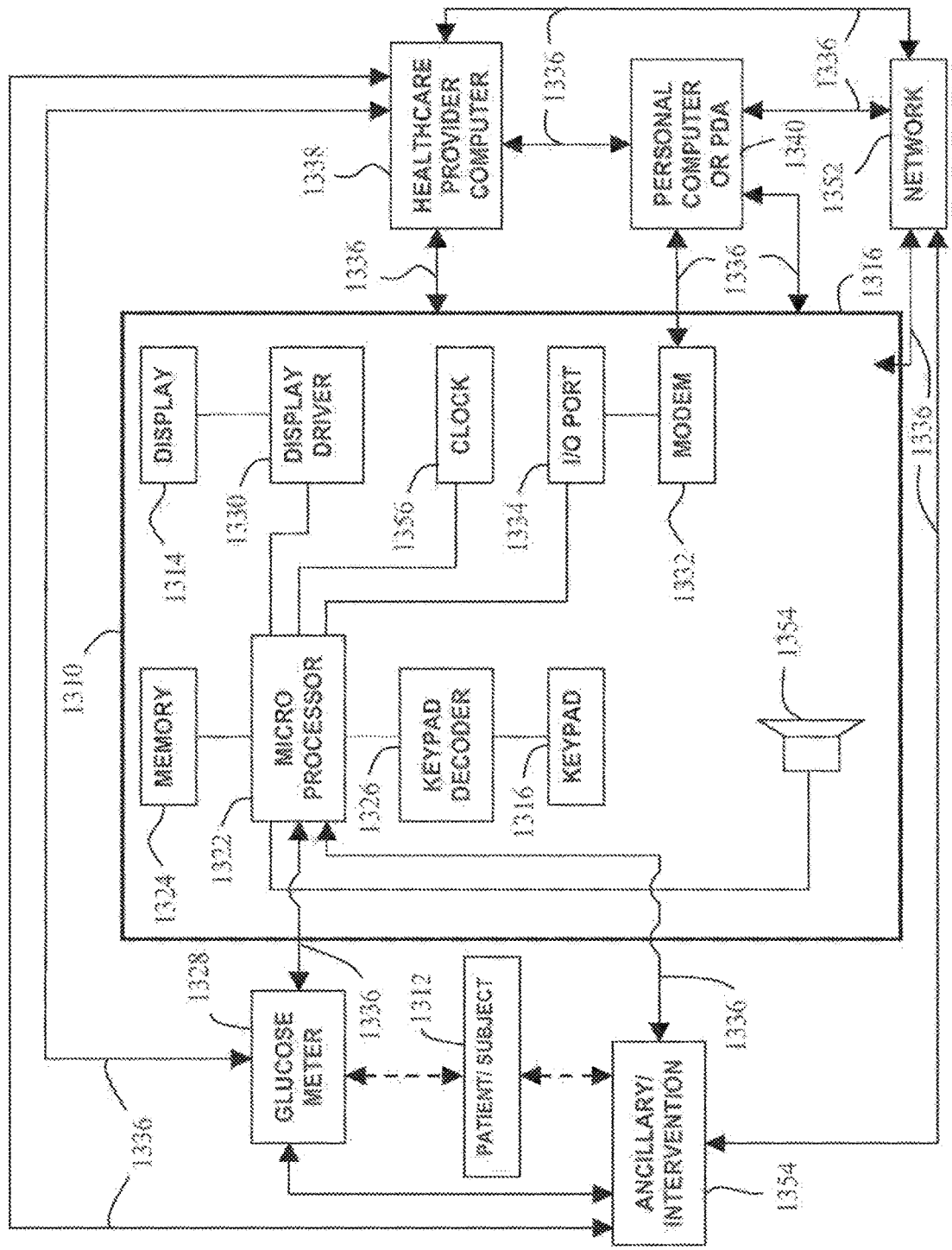
FIG. 13: Provides a schematic block diagram of an aspect of an embodiment of the present invention relating processors, communications links, and systems, for example.

FIGS. 11-13 show block diagrammatic representations of aspects of exemplary embodiments of the present invention. Referring to FIG. 11, there is shown a block diagrammatic representation of the system 1110 essentially comprises the glucose meter 1128 used by a patient 1112 for recording, inter alia, insulin dosage readings and measured blood glucose ("BG") levels. Data obtained by the glucose meter 1128 is preferably transferred through appropriate communication links 1114 or data modem 1132 to a processor, processing station or chip 1140, such as a personal computer, PDA, netbook, laptop, or cellular telephone, or via appropriate Internet portal. For instance data stored may be stored within the glucose meter 1128 and may be directly downloaded into the personal computer or processor 1140 (or PDA, netbook, laptop, etc.) through an appropriate interface cable and then transmitted via the Internet to a processing location. It should be appreciated that the glucose meter 1128 and any of the computer processing modules or storage modules may be integral within a single housing or provided in separate housings. The communication link 1114 may be hardwired or wireless. Examples of hardwired may include, but not limited thereto, cable, wire, fiber optic, and/or telephone wire. Examples of wireless may include, but not limited thereto, Bluetooth, cellular phone link, RF link, and/or infrared link. The modules and components of FIGS. 11-13 may be transmitted to the appropriate or desired computer networks (1152, 1252, 1352) in various locations and sites. The modules and components of FIG. 11 may be transmitted to the appropriate or desired computer networks 1152 in various locations and sites (local and/or remote) via desired or required communication links 1114. Moreover, an ancillary or intervention device(s) or system(s) 1154 may be in communication with the patient as well as the glucose meter and any of the other modules and components shown in FIG. 11. Examples of ancillary device(s) and system(s) may include, but not necessarily limited thereto, any combination of one or more of the following: insulin pump, artificial pancreas, insulin device, pulse oximetry sensor, blood pressure sensor, ICP sensor, EMG sensor, EKG sensor, ECG sensor, ECC sensor, pace maker, and heart rate sensor, needle, ultrasound device, or subcutaneous device (as well as any other biometric sensor or device). It should be appreciated that the ancillary or intervention device(s) or system(s) 1154 and glucose meter 1128 may be any sort of physiological or biological communication with the patients (i.e., subject). This physiological or biological communication may be direct or indirect. An indirect communication (which should not to be confused with an "indirect measurement" as discussed and claimed herein) may include, but not limited thereto, a sample of blood or other biological fluids, or insulin data. A direct communication (which should not to be confused with a "direct measurement" as discussed and claimed herein) may include blood glucose (BG) data.

The glucose meter is common in the industry and includes essentially any device that can function as a BG acquisition mechanism. The BG meter or acquisition mechanism, device, tool or system includes various conventional methods directed towards drawing a blood sample (e.g. by fingerprick) for each test, and a determination of the glucose level using an instrument that reads glucose concentrations by electromechanical methods. Recently, various methods for determining the concentration of blood analytes without drawing blood have been developed. For example, U.S. Pat. No. 5,267,152 to Yang et al. (hereby incorporated by reference) describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al. (of which are hereby incorporated by reference).

U.S. Pat. No. 5,139,023 to Stanley (hereby incorporated by reference) describes a transdermal blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich (hereby incorporated by reference) describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder (of which are hereby incorporated by reference).

In addition, U.S. Pat. No. 5,279,543 to Glikfeld (hereby incorporated by reference) describes the use of iontophoresis to noninvasively sample a substance through skin into a receptacle on the skin surface. Glikfeld teaches that this sampling procedure can be coupled with a glucose-specific biosensor or glucose-specific electrodes in order to monitor blood glucose. Moreover, International Publication No. WO 96/00110 to Tamada (hereby incorporated by reference) describes an iotophoretic apparatus for transdermal monitoring of a target substance, wherein an iotophoretic electrode is used to move an analyte into a collection reservoir and a biosensor is used to detect the target analyte present in the reservoir. Finally, U.S. Pat. No. 6,144,869 to Berner (hereby incorporated by reference) describes a sampling system for measuring the concentration of an analyte present.

Further yet, the BG meter or acquisition mechanism may include indwelling catheters and subcutaneous tissue fluid sampling.

The computer, processor or PDA 1140 may include the software and hardware necessary to process, analyze and interpret the self-recorded or automatically recorded by a clinical assistant device diabetes patient data in accordance with predefined flow sequences and generate an appropriate data interpretation output. The results of the data analysis and interpretation performed upon the stored patient data by the computer or processor 1140 may be displayed in the form of a paper report generated through a printer associated with the personal computer or processor 1140. Alternatively, the results of the data interpretation procedure may be directly displayed on a video display unit associated with the computer or processor 1140. The results additionally may be displayed on a digital or analog display device. The personal computer or processor 1140 may transfer data to a healthcare provider computer 1138 through a communication network 1136. The data transferred through communications network 1136 may include the self-recorded or automated clinical assistant device diabetes patient data or the results of the data interpretation procedure.

FIG. 12 shows a block diagrammatic representation of an alternative embodiment having a diabetes management system that is a patient-operated apparatus or clinical-operated apparatus 1210 having a housing preferably sufficiently compact to enable apparatus 1210 to be hand-held and carried by a patient. A strip guide for receiving a blood glucose test strip (not shown) is located on a surface of housing 1216. Test strip receives a blood sample from the patient 1212. The apparatus may include a microprocessor 1222 and a memory 1224 connected to microprocessor 1222. Microprocessor 1222 is designed to execute a computer program stored in memory 1224 to perform the various calculations and control functions as discussed in greater detail above. A keypad 1216 may be connected to microprocessor 1222 through a standard keypad decoder 1226. Display 1214 may be connected to microprocessor 1222 through a display driver 1230. Display 1214 may be digital and/or analog. Speaker 1254 and a clock 1256 also may be connected to microprocessor 1222. Speaker 1254 operates under the control of microprocessor 1222 to emit audible tones alerting the patient to possible future hypoglycemic or hyperglycemic risks. Clock 1256 supplies the current date and time to microprocessor 1222. Any displays may be visual as well as adapted to be audible.

Memory 1224 also stores blood glucose values of the patient 1212, the insulin dose values, the insulin types, and the parameters used by the microprocessor 1222 to calculate future blood glucose values, supplemental insulin doses, and carbohydrate supplements. Each blood glucose value and insulin dose value may be stored in memory 1224 with a corresponding date and time. Memory 1224 is may be a non-volatile memory, such as an electrically erasable read only memory (EEPROM).

Apparatus 1210 may also include a blood glucose meter 1228 connected to microprocessor 1222. Glucose meter 1228 may be designed to measure blood samples received on blood glucose test strips and to produce blood glucose values from measurements of the blood samples. As mentioned previously, such glucose meters are well known in the art. Glucose meter 1228 is preferably of the type which produces digital values which are output directly to microprocessor 1222. Alternatively, blood glucose meter 1228 may be of the type which produces analog values. In this alternative embodiment, blood glucose meter 1228 is connected to microprocessor 1222 through an analog to digital converter (not shown).

Apparatus 1210 may further include an input/output port 1234, such as a serial port, which is connected to microprocessor 1222. Port 1234 may be connected to a modem 1232 by an interface, such as a standard RS232 interface. Modem 1232 is for establishing a communication link 1248 between apparatus 1210 and a personal computer 1240 or a healthcare provider computer 1238 through a communication link 1248. The modules and components of FIG. 12 may be transmitted to the appropriate or desired computer networks 1252 in various locations and sites (local and/or remote) via desired or required communication links 1248. Moreover, an ancillary or intervention device(s) or system(s) 1254 may be in communication with the patient as well as the glucose meter and any of the other modules and components shown in FIG. 12. Examples of ancillary device(s) and system(s) may include, but not necessarily limited thereto any combination of one or more of the following: insulin pump, artificial pancreas, insulin device, pulse oximetry sensor, blood pressure sensor, ICP sensor, EMG sensor, EKG sensor, ECG sensor, ECC sensor, pace maker, heart rate sensor, needle, ultrasound device, or subcutaneous device (as well as any other biometric sensor or device). It should be appreciated that the ancillary or intervention device(s) or system(s) 1254 and glucose meter 1228 may be any sort of physiological or biological communication with the patients (i.e., subject). This physiological or biological communication may be direct or indirect. An indirect communication may include, but not limited thereto, a sample of blood or other biological fluids. Specific techniques for connecting electronic devices, systems and software through connections, hardwired or wireless, are well known in the art. Another alternative example is "Bluetooth" technology communication.

Alternatively, FIG. 13 shows a block diagrammatic representation of an alternative embodiment having a diabetes management system that is a patient-operated apparatus 1310, similar to the apparatus as shown in FIG. 12, having a housing preferably sufficiently compact to enable the apparatus 1310 to be hand-held and carried by a patient. For example, a separate or detachable glucose meter or BG acquisition mechanism/module 1328. The modules and components of FIG. 13 may be transmitted to the appropriate or desired computer networks 1352 in various locations and sites (local and/or remote) via desired or required communication links 1336. Moreover, an ancillary or intervention device(s) or system(s) 1354 may be in communication with the patient as well as the glucose meter and any of the other modules and components shown in FIG. 13. Examples of ancillary device(s) and system(s) may include, but not necessarily limited thereto any combination of one or more of the following: insulin pump, artificial pancreas, insulin device, pulse oximetry sensor, blood pressure sensor, ICP sensor, EMG sensor, EKG sensor, ECG sensor, ECC sensor, pace maker, heart rate sensor needle, ultrasound device, or subcutaneous device (as well as any other biometric sensor or device). It should be appreciated that the ancillary or intervention device(s) or system(s) 1354 and glucose meter 1328 may be any sort of physiological or biological communication with the patients (i.e., subject). This physiological or biological communication may be direct or indirect. An indirect communication may include, but not limited thereto, a sample of blood or other biological fluids. There are already self-monitoring devices that are capable of directly computing the algorithms disclosed in this application and displaying the results to the patient without transmitting the data to anything else. Examples of such devices are ULTRA SMART by LifeScan, Inc., Milpitas, Calif. and FREESTYLE TRACKER by Therasense, Alameda, Calif.

It should be appreciated that the various blood glucose meters, systems, method and computer program products discussed herein are applicable for CGM. Accordingly, various blood glucose meters, systems, and methods may be utilized with the various embodiments of the present invention. For example, CGM devices may include: Guardian and Paradigm from Medtronic; Freestyle navigator (Abbott Diabetes Care); and Dexcom Seven from Dexcom, Inc., or other available CGM devices.

Accordingly, the embodiments described herein are capable of being implemented over data communication networks such as the internet, making evaluations, estimates, and information accessible to any processor or computer at any remote location, as depicted in FIGS. 11-13 and/or U.S. Pat. No. 5,851,186 to Wood, of which is hereby incorporated by reference herein. Alternatively, patients located at remote locations may have the BG data transmitted to a central healthcare provider or residence, or a different remote location.

It should be appreciated that any of the components/modules discussed in FIGS. 11-13 may be integrally contained within one or more housings or separated and/or duplicated in different housings. Similarly, any of the components discussed in FIGS. 11-13 may be duplicated more than once. Moreover, various components and modules may be adapted to replace another component or module to perform the intended function.

It should also be appreciated that any of the components/modules present in FIGS. 11-13 may be in direct or indirect communication with any of the other components/modules.

It should be appreciated that the healthcare provide computer module as depicted in FIGS. 11-13 may be any location, person, staff, physician, caregiver, system, device or equipment at any healthcare provider, hospital, clinic, university, vehicle, trailer, or home, as well as any other location, premises, or organization as desired or required.

It should be appreciated that as discussed herein, a patient or subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example. The patient or subject may be applicable for, but not limited thereto, any desired or required treatment, study, diagnosis, monitoring, tracking, therapy or care.

Figure 14:
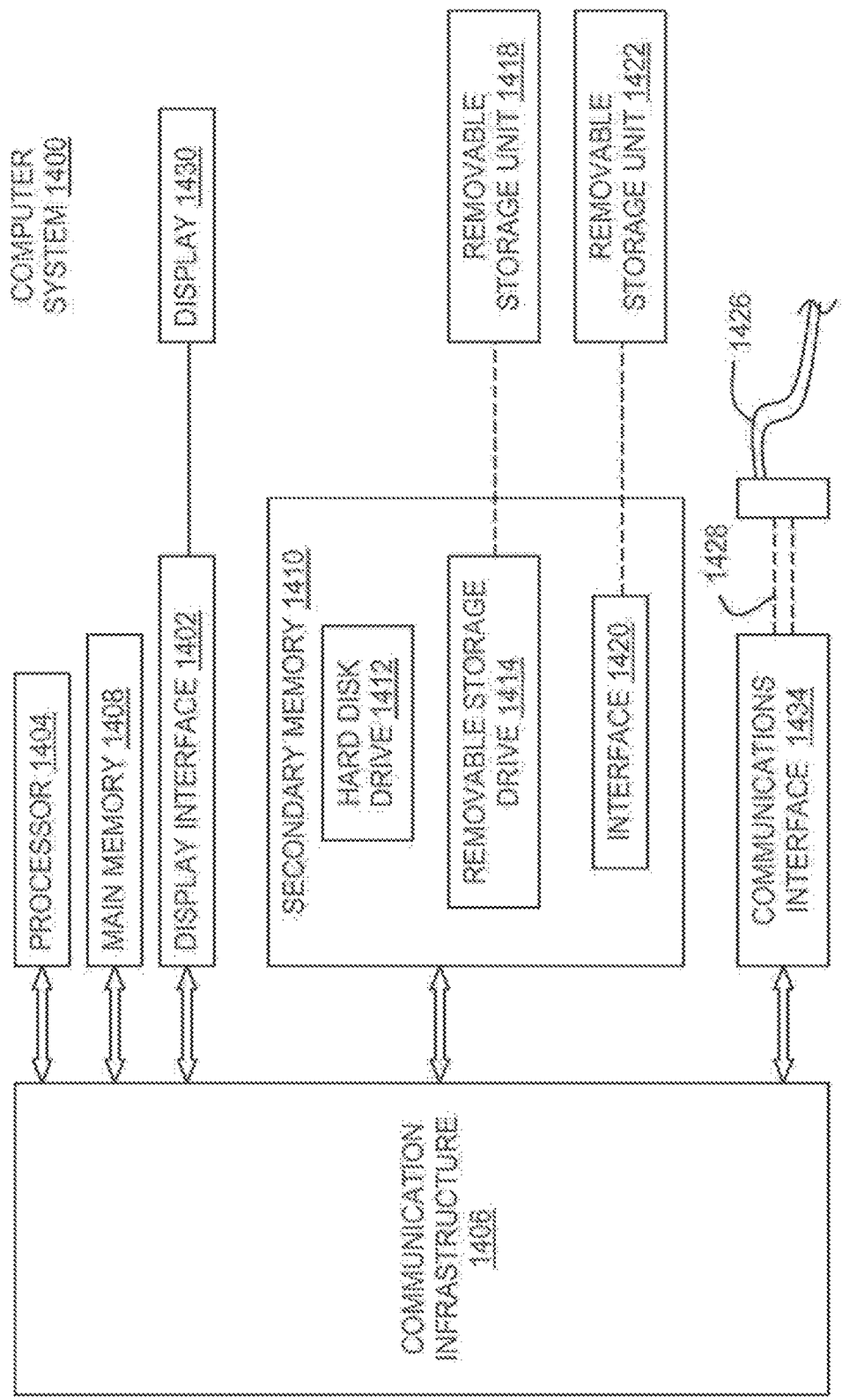
FIG. 14: Provides a schematic block diagram for an aspect of a system or related method of an aspect of an embodiment of the present invention.

FIG. 14 is a functional block diagram for a computer system 1400 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs), personal computer, laptop, netbook, network, or the like equipped with adequate memory and processing capabilities. In an example embodiment, the invention was implemented in software running on a general purpose computer as illustrated in FIG. 14. The computer system 1400 may includes one or more processors, such as processor 1404. The Processor 1404 is connected to a communication infrastructure 1406 (e.g., a communications bus, cross-over bar, or network). The computer system 1400 may include a display interface 1402 that forwards graphics, text, and/or other data from the communication infrastructure 1406 (or from a frame buffer not shown) for display on the display unit 1430. Display unit 1430 may be digital and/or analog.

The computer system 1400 may also include a main memory 1408, preferably random access memory (RAM), and may also include a secondary memory 1410. The secondary memory 1410 may include, for example, a hard disk drive 1412 and/or a removable storage drive 1414, representing a floppy disk drive, a magnetic tape drive, an optical disk drive, a flash memory, etc. The removable storage drive 1414 reads from and/or writes to a removable storage unit 1418 in a well known manner. Removable storage unit 1418, represents a floppy disk, magnetic tape, optical disk, etc. which is read by and written to by removable storage drive 1414. As will be appreciated, the removable storage unit 1418 includes a computer usable storage medium having stored therein computer software and/or data.

In alternative embodiments, secondary memory 1410 may include other means for allowing computer programs or other instructions to be loaded into computer system 1400. Such means may include, for example, a removable storage unit 1422 and an interface 1420. Examples of such removable storage units/interfaces include a program cartridge and cartridge interface (such as that found in video game devices), a removable memory chip (such as a ROM, PROM, EPROM or EEPROM) and associated socket, and other removable storage units 1422 and interfaces 1420 which allow software and data to be transferred from the removable storage unit 1422 to computer system 1400.

The computer system 1400 may also include a communications interface 1424. Communications interface 1424 allows software and data to be transferred between computer system 1400 and external devices. Examples of communications interface 1424 may include a modem, a network interface (such as an Ethernet card), a communications port (e.g., serial or parallel, etc.), a PCMCIA slot and card, a modem, etc. Software and data transferred via communications interface 1424 are in the form of signals 1428 which may be electronic, electromagnetic, optical or other signals capable of being received by communications interface 1424. Signals 1428 are provided to communications interface 1424 via a communications path (i.e., channel) 1426. Channel 1426 (or any other communication means or channel disclosed herein) carries signals 1428 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 1414, a hard disk installed in hard disk drive 1412, and signals 1428. These computer program products ("computer program medium" and "computer usable medium") are means for providing software to computer system 1400. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 1408 and/or secondary memory 1410. Computer programs may also be received via communications interface 1424. Such computer programs, when executed, enable computer system 1400 to perform the features of the present invention as discussed herein. In particular, the computer programs, when executed, enable processor 1404 to perform the functions of the present invention. Accordingly, such computer programs represent controllers of computer system 1400.

In an embodiment where the invention is implemented using software, the software may be stored in a computer program product and loaded into computer system 1400 using removable storage drive 1414, hard drive 1412 or communications interface 1424. The control logic (software or computer program logic), when executed by the processor 1404, causes the processor 1404 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

Unless defined otherwise, all technical terms used herein have the same meanings as commonly understood by one of ordinary skill in the art of treating diabetes. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices, equipment, or drugs has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology. Further, while some theoretical considerations have been advanced in furtherance of providing an understanding, for example, of the quantitative interrelationships among carbohydrate consumption, glucose levels, and insulin levels, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary.

Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

REFERENCES

The devices, systems, computer program products, and methods of various embodiments of the invention disclosed herein may utilize aspects disclosed in the following references, applications, publications and patents and which are hereby incorporated by reference herein in their entirety:

1. Stephen D. Patek, Marc Breton, and Boris P. Kovatchev, "Control of Hypoglycemia via Estimation of Active Insulin, Glucose Forecasts, and Risk-Based Insulin Reduction," Abstract in the Proceeding of the 2nd International Conference on Advanced Technologies & Treatments for Diabetes (ATTD), Athens, Greece, Feb. 25-28, 2009.
2. Stephen D. Patek, Marc Breton, Colleen Hughes, and Boris P. Kovatchev, "Control of Hypoglycemia via Estimation of Active Insulin, Glucose Forecasts, and Risk-Based Insulin Reduction," Poster presented at the 2nd International Conference on Advanced Technologies & Treatments for Diabetes (ATTD), Athens, Greece, Feb. 25-28, 2009.
3. Stephen D. Patek, "Status of the Artificial Pancreas," Keynote Presentation at the Annual Conference of the American Society for Artificial Internal Organs, Dallas, Tex., May 30, 2009.
4. Stephen D. Patek and Boris P. Kovatchev, "Artificial Pancreas: State of the Art, Control and Systems Engineering Challenges," Invited Presentation to the Langer Group at MIT, Cambridge, Mass., Oct. 5, 2009.
5. Stephen D. Patek, Eyal Dassau, Marc Breton, Howard Zisser, Boris Kovatchev, Francis J. Doyle III, "Safety Supervision Module in Open- and Closed-Loop Control of Diabetes," Abstract in the proceedings of the Diabetes Technology Meeting, November 2009.
6. Stephen D. Patek, Eyal Dassau, Marc Breton, Howard Zisser, Boris Kovatchev, Francis J. Doyle III, "Safety Supervision Module in Open- and Closed-Loop Control of Diabetes," Poster presented at the Diabetes Technology Meeting, November 2009.
7. B. Buckingham, E. Cobry, P. Clinton, V. Gage, K. Caswell, E. Kunselman, F. Cameron, and H. P. Chase, "Preventing hypoglycemia using predictive alarm algorithms and insulin pump suspension," *Diabetes Technology and Therapeutics*, vol. 11(2), pp. 93-97, 2009.

8. E. Cengiz, K. L. Swan, W. V. Tamborlane, G. M. Steil, A. T. Steffen and S. A. Weinzimer, "Is an Automatic Pump Suspension Feature Safe for Children with Type 1 Diabetes? An Exploratory Analysis with Closed-Loop System", Diabetes Technology & Therapeutics, 11, 4, 207-210, 2009.
9. B. P. Kovatchev, D. J. Cox, L. A. Gonder-Frederick, and W. L. Clarke, "Symmetrization of the blood glucose measurement scale and its applications," *Diabetes Care*, vol. 20, pp. 1655-1658, 1997.
10. PCT/US2008/082063, entitled "Model Predictive Control Based Method for Closed-Loop Control of Insulin Delivery in Diabetes Using Continuous Glucose Sensing", filed Oct. 31, 2008.
11. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008.
12. PCT/US2008/067725, entitled "Method, System and Computer Simulation Environment for Testing of Monitoring and Control Strategies in Diabetes," filed Jun. 20, 2008.
13. PCT/US2008/067723, entitled "LQG Artificial Pancreas Control System and Related Method", filed on Jun. 20, 2008.
14. U.S. Ser. No. 12/516,044, filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes;"
15. PCT/US2007/085588 not yet published filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes;"
16. U.S. Ser. No. 11/943,226, filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes;"
17. U.S. patent application Ser. No. 11/578,831, filed Oct. 18, 2006 entitled "Method, System and Computer Program Product for Evaluating the Accuracy of Blood Glucose Monitoring Sensors/Devices".
18. PCT International Application Serial No. PCT/US2005/013792, filed Apr. 21, 2005, entitled "Method, System, and Computer Program Product for Evaluation of the Accuracy of Blood Glucose Monitoring Sensors/Devices;"
19. PCT International Application Serial No. PCT/US01/09884, filed Mar. 29, 2001, entitled "Method, System, and Computer Program Product for Evaluation of Glycemic Control in Diabetes Self-Monitoring Data;"
20. U.S. Pat. No. 7,025,425 B2 issued Apr. 11, 2006, entitled "Method, System, and Computer Program Product for the Evaluation of Glycemic Control in Diabetes from Self-Monitoring Data;"
21. U.S. patent application Ser. No. 11/305,946 filed Dec. 19, 2005 entitled "Method, System, and Computer Program Product for the Evaluation of Glycemic Control in Diabetes from Self-Monitoring Data" (Publication No. 2006/0094947);
22. PCT International Application Serial No. PCT/US2003/025053, filed Aug. 8, 2003, entitled "Method, System, and Computer Program Product for the Processing of Self-Monitoring Blood Glucose (SMBG) Data to Enhance Diabetic Self-Management;"
23. U.S. patent application Ser. No. 10/524,094 filed Feb. 9, 2005 entitled "Managing and Processing Self-Monitoring Blood Glucose" (Publication No. 2005/214892);
24. U.S. Ser. No. 12/065,257, filed Aug. 29, 2008, entitled "Accuracy of Continuous Glucose Sensors;"
25. PCT International Application Serial No PCT/US2006/033724, filed Aug. 29, 2006, entitled "Method for Improvising Accuracy of Continuous Glucose Sensors and a Continuous Glucose Sensor Using the Same;"
26. U.S. Ser. No. 12/159,891, filed Jul. 2, 2008, entitled "Method, System and Computer Program Product for Evaluation of Blood Glucose Variability in Diabetes from Self-Monitoring Data;"
27. PCT International Application No. PCT/US2007/000370, filed Jan. 5, 2007, entitled "Method, System and Computer Program Product for Evaluation of Blood Glucose Variability in Diabetes from Self-Monitoring Data;"
28. U.S. patent application Ser. No. 11/925,689 and PCT International Patent Application No. PCT/US2007/082744, both filed Oct. 26, 2007, entitled "For Method, System and Computer Program Product for Real-Time Detection of Sensitivity Decline in Analyte Sensors;"
29. U.S. Ser. No. 10/069,674, filed Feb. 22, 2002, entitled "Method and Apparatus for Predicting the Risk of Hypoglycemia;"
30. PCT International Application No. PCT/US00/22886, filed Aug. 21, 2000, entitled "Method and Apparatus for Predicting the Risk of Hypoglycemia;"
31. U.S. Pat. No. 6,923,763 B1, issued Aug. 2, 2005, entitled "Method and Apparatus for Predicting the Risk of Hypoglycemia;" and
32. Kovatchev B P, Straume M, Cox D J, Farhy L S. Risk analysis of blood glucose data: A quantitative approach to optimizing the control of insulin dependent diabetes. *J of Theoretical Medicine*, 3:1-10, 2001.

The invention claimed is:

1. A method of preventing or mitigating hypoglycemia in a subject, the method comprising:
   receiving measurements from a metabolic measurement device providing direct metabolic measurements of a subject;
   assessing a risk of hypoglycemia in the subject based at least on the received measurements from the metabolic measurement device providing the direct metabolic measurements of the subject;
   determining an insulin attenuation factor, the determination of the insulin attenuation factor occurring after the assessing of the risk of hypoglycemia;
   providing one or more options as an output addressing the assessed risk of hypoglycemia in the subject, the output instructing the subject to:
   a) take no action;
   b) attenuate insulin delivery using the determined insulin attenuation factor;
   c) take additional intervention; or
   d) attenuate insulin delivery using the determined insulin attenuation factor and take additional intervention.

2. The method of claim 1, comprising:
   calculating the attenuation factor based on the assessed risk of hypoglycemia.

3. The method of claim 2, comprising:
   implementing a safety supervision function that calculates the attenuation factor.

4. The method of claim 1, comprising:
evaluating a risk of hypoglycemia based on the assessed risk of hypoglycemia.

5. A system for preventing or mitigating hypoglycemia in a subject, the system comprising one or more processors configured for:
receiving measurements from a metabolic measurement device providing direct metabolic measurements of a subject;
assessing a risk of hypoglycemia in the subject based at least on the received measurements from the metabolic measurement device providing the direct metabolic measurements of the subject;
determining an insulin attenuation factor, the determination of the insulin attenuation factor occurring after the assessing of the risk of hypoglycemia;
providing one or more options as an output addressing the assessed risk of hypoglycemia in the subject, the output instructing the subject to:
a) take no action;
b) attenuate insulin delivery using the determined insulin attenuation factor;
c) take additional intervention; or
d) attenuate insulin delivery using the determined insulin attenuation factor and take additional intervention.

6. The system of claim 5, wherein:
the one or more processors include a glucose meter, an insulin pump, an artificial pancreas, an insulin device, a personal computer, a PDA, a netbook, a laptop, and/or a cellular telephone.

7. The system of claim 5, wherein:
the one or more processors calculates the attenuation factor based on the assessed risk of hypoglycemia.

8. The system of claim 7, wherein:
the one or more processors implements a safety supervision function that calculates the attenuation factor.

9. The system of claim 5, wherein:
the one or more processors evaluates a risk of hypoglycemia based on the assessed risk of hypoglycemia.

10. A non-transitory computer readable recording medium encoded with a computer program including instructions causing preventing or mitigating hypoglycemia in a subject via one or more processors, the program causing the one or more processors to:
receive measurements from a metabolic measurement device providing direct metabolic measurements of a subject;
assess a risk of hypoglycemia in the subject based at least on the received measurements from the metabolic measurement device providing the direct metabolic measurements of the subject;
determine an insulin attenuation factor, the determination of the insulin attenuation factor occurring after the assessing of the risk of hypoglycemia;
provide one or more options as an output addressing the assessed risk of hypoglycemia in the subject, the output instructing the subject to:
a) take no action;
b) attenuate insulin delivery using the determined insulin attenuation factor;
c) take additional intervention; or
d) attenuate insulin delivery using the determined insulin attenuation factor and take additional intervention.

11. The non-transitory computer readable recording medium of claim 10, wherein:
the one or more processors include a glucose meter, an insulin pump, an artificial pancreas, an insulin device, a personal computer, a PDA, a netbook, a laptop, and/or a cellular telephone.

12. The non-transitory computer readable recording medium of claim 10, wherein:
the program causes the one or more processors to calculate the attenuation factor based on the assessed risk of hypoglycemia.

13. The non-transitory computer readable recording medium of claim 12, wherein:
the program causes the one or more processors to implement a safety supervision function that calculates the attenuation factor.

14. The non-transitory computer readable recording medium of claim 10, wherein:
the program causes the one or more processors to evaluate a risk of hypoglycemia based on the assessed risk of hypoglycemia.

* * * * *